(12) United States Patent
Zhai et al.

(10) Patent No.: US 11,014,888 B2
(45) Date of Patent: May 25, 2021

(54) CRYSTALLINE FORM OF ALKYNYL PYRIDINE PROLYL HYDROXYLASE INHIBITOR AND METHOD FOR PREPARING SAME

(71) Applicant: JIANGSU HENGRUI MEDICINE CO., LTD., Jiangsu (CN)

(72) Inventors: Lijuan Zhai, Jiangsu (CN); Zhenxing Du, Jiangsu (CN); Likun Wang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/757,333

(22) PCT Filed: Oct. 24, 2018

(86) PCT No.: PCT/CN2018/111630
§ 371 (c)(1),
(2) Date: Apr. 17, 2020

(87) PCT Pub. No.: WO2019/080865
PCT Pub. Date: May 2, 2019

(65) Prior Publication Data
US 2020/0299240 A1   Sep. 24, 2020

(30) Foreign Application Priority Data

Oct. 25, 2017  (CN) .......................... 201711008888.3
Dec. 4, 2017   (CN) .......................... 201711261104.8

(51) Int. Cl.
*C07D 213/81*    (2006.01)
(52) U.S. Cl.
CPC ........ *C07D 213/81* (2013.01); *C07B 2200/13* (2013.01)
(58) Field of Classification Search
CPC .......................... C07D 213/81; C07B 2200/13
See application file for complete search history.

(56) References Cited

U.S. PATENT DOCUMENTS

2018/0305317 A1*  10/2018  You ...................... C07D 405/12

FOREIGN PATENT DOCUMENTS

| CN | 105130888 | 12/2015 |
| WO | 2017059623 A1 | 4/2017 |

OTHER PUBLICATIONS

International Search Report, International Application No. PCT/CN2018/111630, Jiangsu Hengrui Medicine Co., Ltd., Jan. 30, 2019.
Dikow et al., "How should we manage anaemia in patents with diabetes?,", Nephrol Dial Transplant 17 (2002), 67-72.
Rabinowitz, "Inhibition of Hypoxia-Inducible Factor Prolyl Hydroxylase Domain Oxygen Sensors: Tricking the Body into Mounting Orchestrated Survival and Repair Responses," Journal of Medicinal Chemistry 56(2013), 9369-9402.

* cited by examiner

*Primary Examiner* — Timothy R Rozof
(74) *Attorney, Agent, or Firm* — Ice Miller LLP

(57) ABSTRACT

A crystalline form of alkynyl pyridine prolyl hydroxylase inhibitor and a method for preparing same are described. Specifically, a new crystalline form of alkynyl pyridine prolyl hydroxylase inhibitor as represented by formula (I) is described. The new crystalline form of the present invention has good stability and may be better used for clinical treatment.

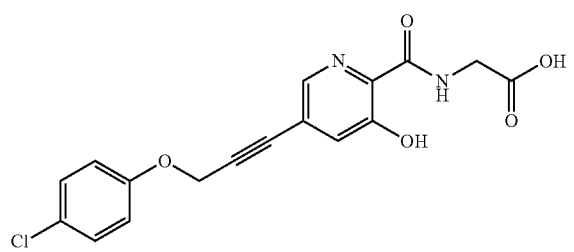

(I)

17 Claims, 14 Drawing Sheets

CRYSTALLINE FORM OF ALKYNYL PYRIDINE PROLYL HYDROXYLASE INHIBITOR AND METHOD FOR PREPARING SAME

CROSS-REFERENCE TO RELATED APPLICATIONS

This application is a Section 371 of International Patent Application No. PCT/CN2018/111630, filed Oct. 24, 2018, which was published in the Chinese language on May 2, 2019, under International Publication No. WO 2019/080865 A1, which claims priority under 35 U.S.C. § 119(b) to Chinese Patent Application No. 201711008888.3, filed Oct. 25, 2017, and Chinese Patent Application No. 201711261104.8, filed Dec. 4, 2017, the disclosure of all of which are incorporated herein by reference in their entireties.

FIELD OF THE INVENTION

The present invention relates to a crystal form of an alkynyl pyridines prolyl hydroxylase inhibitor and a method for preparing the same, as well as a use thereof in the preparation of a medicament for treating a prolyl hydroxylase-mediated disease.

BACKGROUND OF THE INVENTION

Anemia generally refers to any abnormality in hemoglobin or red blood cells that leads to reduced oxygen levels in the blood. Anemia can also develop in association with chronic diseases, such as chronic infection, neoplastic diseases, chronic inflammation, including disorders of consequent inflammatory suppression of marrow, etc. Anemia of chronic disease, for example anemia in chronic kidney disease, is one of the most common syndromes in medicine. The main cause of anemia in chronic kidney disease is insufficient secretion of erythropoietin (EPO) (*Nephrol Dial Transplant* 17 (2002)2-7). The insufficient secretion of EPO can hinder the production of red blood cells, resulting in the occurrence of anemia. The expression and secretion of EPO are regulated by the transcription factor hypoxia inducible factor (HIF). The HIF protein with complete transcription function is composed of two subunits HIF-α and HIF-β, of which HIF-α is regulated by prolyl hydroxylase (PHD) that can hydroxylate HIF-α to promote its degradation. Inside the human body, prolyl hydroxylase 2 (PHD2) is the most dominant subtype that regulates HIF levels (*Journal of Medicinal Chemistry* 56 (2013)9369-9402). When the activity of prolyl hydroxylase (PHD) in vivo is inhibited, the HIF-α subunit can be stabilized in vivo, so that it enters the nucleus, and binds to the HIF-β subunit in the nucleus to form a stable HIF dimer. The dimer further causes the expression of downstream genes, thereby promoting the expression and secretion of EPO. Therefore, the inhibition of activity of prolyl hydroxylase can increase HIF-α level and promote the production of EPO, thereby promoting the maturation of red blood cells, enhancing the capacity of blood in delivering oxygen, and improving anemia or ischemic symptoms.

WO2017059623 discloses a novel class of alkynyl pyridines prolyl hydroxylase inhibitors. Among them, the compound of formula (I), whose chemical name is 2-(3-hydroxy-5-(3-p-chlorophenoxypropyn-1-yl))picolinamido acetic acid, shows an excellent inhibition effect on prolyl hydroxylase, and is a potential new drug for treating chronic anemia.

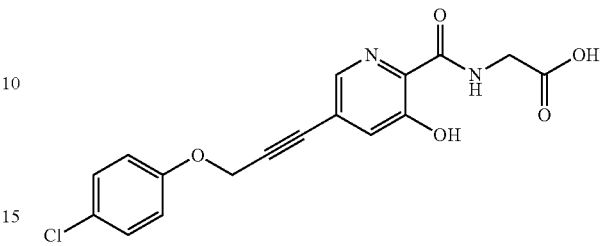

(I)

It is well known that a compound can exist in a variety of crystal forms. The crystal structure of a pharmaceutically active ingredient often affects the chemical and physical stability of the drug. Different crystallization conditions, preparation methods and storage conditions may lead to changes in the crystal structure of a compound, and sometimes accompanying production of other crystal forms. In general, an amorphous drug product does not have a regular crystal structure, and often has other defects such as poor product stability, difficult filtration, easy agglomeration and poor liquidity, which often lead to difficulties in production and scaleup. The stability of existing crystal forms needs to be improved. Therefore, it is necessary to improve the various properties of the compound. There is a need to find novel crystal forms with high purity and good chemical stability.

SUMMARY OF THE INVENTION

The object of the present invention is to provide novel crystal forms of the compound of formula (I), which have good crystal form stability and chemical stability, and can be better applied in clinical practice.

In an aspect, the present invention provides crystal form A of the compound of formula (I), characterized in that: the crystal form A has an X-ray powder diffraction spectrum, which is obtained by using Cu-Kα radiation and represented by diffraction angle 2θ angle, in which there are characteristic peaks at 2θ angles of 10.44, 14.01, 15.27, 18.03, 21.18, 22.66, 22.96, 23.85, 27.68 and 30.37.

In a preferred embodiment, the present invention provides crystal form A of the compound of formula (I), characterized in that: the crystal form A has an X-ray powder diffraction spectrum, which is obtained by using Cu-Kα radiation and represented by diffraction angle 2θ angle, in which there are characteristic peaks at 2θ angles of 10.44, 11.78, 14.01, 15.27, 18.03, 21.18, 22.66, 22.96, 23.85, 24.78, 25.29, 27.68, 30.37 and 36.38.

In a preferred embodiment, the present invention provides crystal form A of the compound of formula (I), characterized in that: the crystal form A has an X-ray powder diffraction spectrum, which is obtained by using Cu-Kα radiation and represented by diffraction angle 2θ angle, in which there are characteristic peaks at 2θ angles of 10.44, 11.78, 14.01, 15.27, 18.03, 21.18, 22.66, 22.96, 23.85, 24.78, 25.29, 26.76, 27.68, 28.36, 30.37, 32.07, 36.38 and 41.67.

In a preferred embodiment, the present invention provides crystal form A of the compound of formula (I), characterized in that: the crystal form A has an X-ray powder diffraction spectrum, which is obtained by using Cu-Kα radiation and represented by diffraction angle 2θ angle, in which there are characteristic peaks at 2θ angles of 10.444, 11.782, 14.008, 15.268, 18.034, 21.183, 22.656, 22.958, 23.849, 24.775, 25.291, 26.760, 27.675, 28.359, 30.372, 32.074, 36.379 and 41.668.

In a preferred embodiment, the present invention provides crystal form A of the compound of formula (I), characterized in that: the crystal form A has an X-ray powder diffraction spectrum as shown in FIG. 1, which is obtained by using Cu-Kα radiation.

The present invention further provides a method for preparing the crystal form A of the compound of formula (I), comprising the steps of:

(1) method I, dissolving the compound of formula (I) in an appropriate amount of solvent to precipitate a crystal, and filtering the resulting crystal to obtain the desired crystal form A, wherein the solvent can be one or more of dimethyl sulfoxide, tetrahydrofuran, propylene glycol methyl ether, methanol, acetonitrile, ethyl acetate, ethanol, water and isopropanol; or (2) method II, adding the compound of formula (I) into an appropriate amount of solvent, slurrying the mixture, and filtering the resulting crystal to obtain the desired crystal form A, wherein the solvent can be one or more of water, cyclohexane, methanol and ethanol.

In another aspect, the present invention provides crystal form B of the compound of formula (I), characterized in that: the crystal form B has an X-ray powder diffraction spectrum, which is obtained by using Cu-Kα radiation and represented by diffraction angle 2θ angle, in which there are characteristic peaks at 2θ angles of 6.34, 12.17, 14.75, 17.84, 20.27, 20.89, 22.17, 22.85, 24.49, 27.46, 27.86 and 29.19.

In a preferred embodiment, the present invention provides crystal form B of the compound of formula (I), characterized in that: the crystal form B has an X-ray powder diffraction spectrum, which is obtained by using Cu-Kα radiation and represented by diffraction angle 2θ angle, in which there are characteristic peaks at 2θ angles of 6.34, 12.17, 12.84, 14.75, 17.84, 19.35, 20.27, 20.89, 22.17, 22.85, 23.68, 24.49, 25.03, 27.46, 27.86, 28.54, 29.19 and 31.12.

In a preferred embodiment, the present invention provides crystal form B of the compound of formula (I), characterized in that: the crystal form B has an X-ray powder diffraction spectrum, which is obtained by using Cu-Kα radiation and represented by diffraction angle 2θ angle, in which there are characteristic peaks at 2θ angles of 6.34, 12.17, 12.84, 14.75, 17.84, 19.35, 20.27, 20.89, 22.17, 22.85, 23.68, 24.49, 25.03, 26.00, 27.46, 27.86, 28.54, 29.19, 29.99, 31.12, 32.62 and 40.36.

In a preferred embodiment, the present invention provides crystal form B of the compound of formula (I), characterized in that: the crystal form B has an X-ray powder diffraction spectrum, which is obtained by using Cu-Kα radiation and represented by diffraction angle 2θ angle, in which there are characteristic peaks at 2θ angles of 6.341, 12.165, 12.836, 14.747, 17.840, 19.345, 20.273, 20.894, 22.172, 22.852, 23.675, 24.490, 25.033, 26.001, 27.457, 27.856, 28.542, 29.187, 29.994, 31.124, 32.616 and 40.361.

In a preferred embodiment, the present invention provides crystal form B of the compound of formula (I), characterized in that: the crystal form B has an X-ray powder diffraction spectrum as shown in FIG. 2, which is obtained by using Cu-Kα radiation.

The crystal form B shows an excellent chemical stability under different placement conditions (for example, 40° C., humidity 75%, open/sealed; 25° C., humidity 60%, open; or 2-6° C., sealed), and has not been substantially degraded.

The present invention further provides a method for preparing the crystal form B of the compound of formula (I), comprising the steps of:

(1) method I, dissolving the compound of formula (I) in an appropriate amount of acetic acid to precipitate a crystal, and filtering the resulting crystal to obtain the desired crystal form B; or (2) method II, adding the compound of formula (I) into an appropriate amount of solvent, slurrying the mixture, and filtering the resulting crystal to obtain the desired crystal form B, wherein the solvent can be one or more of dichloromethane, 1,2-dichloroethane, n-heptane, isopropanol, isoamylol, trifluoroethanol and nitromethane.

In another aspect, the present invention provides crystal form C of the compound of formula (I), characterized in that: the crystal form C has an X-ray powder diffraction spectrum, which is obtained by using Cu-Kα radiation and represented by diffraction angle 2θ angle, in which there are characteristic peaks at 2θ angles of 6.33, 9.71, 14.04, 14.70, 17.79, 20.84, 21.19, 22.16, 22.85, 23.68, 24.53, 27.47 and 28.73.

In a preferred embodiment, the present invention provides crystal form C of the compound of formula (I), characterized in that: the crystal form C has an X-ray powder diffraction spectrum, which is obtained by using Cu-Kα radiation and represented by diffraction angle 2θ angle, in which there are characteristic peaks at 2θ angles of 6.33, 9.71, 14.04, 14.70, 17.79, 19.35, 20.84, 21.19, 22.16, 22.85, 23.68, 24.53, 24.93, 27.47, 28.73 and 29.23.

In a preferred embodiment, the present invention provides crystal form C of the compound of formula (I), characterized in that: the crystal form C has an X-ray powder diffraction spectrum, which is obtained by using Cu-Kα radiation and represented by diffraction angle 2θ angle, in which there are characteristic peaks at 2θ angles of 6.33, 9.71, 14.04, 14.70, 17.79, 19.35, 20.22, 20.84, 21.19, 22.16, 22.85, 23.68, 24.53, 24.93, 27.47, 28.73, 29.23 and 31.06.

In a preferred embodiment, the present invention provides crystal form C of the compound of formula (I), characterized in that: the crystal form C has an X-ray powder diffraction spectrum, which is obtained by using Cu-Kα radiation and represented by diffraction angle 2θ angle, in which there are characteristic peaks at 2θ angles of 6.333, 9.713, 14.040, 14.703, 17.791, 19.347, 20.222, 20.840, 21.193, 22.163, 22.847, 23.678, 24.527, 24.926, 27.472, 28.727, 29.232 and 31.060.

In a preferred embodiment, the present invention provides crystal form C of the compound of formula (I), characterized in that: the crystal form C has an X-ray powder diffraction spectrum as shown in FIG. 3, which is obtained by using Cu-Kα radiation.

The present invention further provides a method for preparing the crystal form C of the compound of formula (I), comprising the steps of:

dissolving the compound of formula (I) in an appropriate amount of a mixed solvent of water and methanol to precipitate a crystal, and filtering the resulting crystal to obtain the desired crystal form C.

In another aspect, the present invention provides crystal form D of the compound of formula (I), characterized in that: the crystal form D has an X-ray powder diffraction spectrum, which is obtained by using Cu-Kα radiation and represented by diffraction angle 2θ angle, in which there are characteristic peaks at 2θ angles of 7.28, 9.67, 9.72, 9.79, 14.72, 15.37, 17.67, 19.56, 21.21, 23.79, 26.88 and 29.85.

In a preferred embodiment, the present invention provides crystal form D of the compound of formula (I), characterized in that: the crystal form D has an X-ray powder diffraction spectrum, which is obtained by using Cu-Kα radiation and represented by diffraction angle 2θ angle, in which there are characteristic peaks at 2θ angles of 7.28, 9.67, 9.72, 9.79, 14.72, 15.37, 17.67, 19.56, 20.76, 21.21, 23.79, 25.13, 26.88, 29.85, 31.58 and 33.43.

In a preferred embodiment, the present invention provides crystal form D of the compound of formula (I), characterized in that: the crystal form D has an X-ray powder diffraction spectrum, which is obtained by using Cu-Kα radiation and represented by diffraction angle 2θ angle, in which there are characteristic peaks at 2θ angles of 7.28, 9.67, 9.72, 9.79, 14.72, 15.37, 17.67, 19.56, 20.76, 21.21, 23.79, 25.13, 26.25, 26.88, 28.36, 29.85, 31.58, 33.43 and 35.38.

In a preferred embodiment, the present invention provides crystal form D of the compound of formula (I), characterized in that: the crystal form D has an X-ray powder diffraction spectrum, which is obtained by using Cu-Kα radiation and represented by diffraction angle 2θ angle, in which there are characteristic peaks at 2θ angles of 7.281, 9.673, 9.724, 9.794, 14.723, 15.369, 17.665, 19.556, 20.756, 21.207, 23.785, 25.125, 26.247, 26.882, 28.326, 28.360, 29.853, 31.578, 33.425 and 35.377.

In a preferred embodiment, the present invention provides crystal form D of the compound of formula (I), characterized in that: the crystal form D has an X-ray powder diffraction spectrum as shown in FIG. 4, which is obtained by using Cu-Kα radiation.

The present invention further provides a method for preparing the crystal form D of the compound of formula (I), comprising the steps of:

dissolving the compound of formula (I) in an appropriate amount of 1,4-dioxane to precipitate a crystal, and filtering the resulting crystal to obtain the desired crystal form D.

In another aspect, the present invention provides crystal form H of the compound of formula (I), characterized in that: the crystal form H has an X-ray powder diffraction spectrum, which is obtained by using Cu-Kα radiation and represented by diffraction angle 2θ angle, in which there are characteristic peaks at 2θ angles of 7.79, 15.69, 16.17, 16.21, 17.54, 19.63, 23.95, 25.59, 25.64 and 31.74.

In a preferred embodiment, the present invention provides crystal form H of the compound of formula (I), characterized in that: the crystal form H has an X-ray powder diffraction spectrum, which is obtained by using Cu-Kα radiation and represented by diffraction angle 2θ angle, in which there are characteristic peaks at 2θ angles of 7.14, 7.79, 11.01, 15.69, 16.17, 16.21, 17.54, 19.63, 23.95, 23.98, 24.95, 25.59, 25.64 and 31.74.

In a preferred embodiment, the present invention provides crystal form H of the compound of formula (I), characterized in that: the crystal form H has an X-ray powder diffraction spectrum, which is obtained by using Cu-Kα radiation and represented by diffraction angle 2θ angle, in which there are characteristic peaks at 2θ angles of 7.14, 7.79, 11.01, 14.22, 15.69, 16.17, 16.21, 17.54, 19.63, 20.55, 22.20, 23.95, 23.98, 24.95, 25.59, 25.64, 27.64, 28.50, 29.72, 30.55, 31.74, 32.72, 35.04, 35.44 and 40.18.

In a preferred embodiment, the present invention provides crystal form H of the compound of formula (I), characterized in that: the crystal form H has an X-ray powder diffraction spectrum, which is obtained by using Cu-Kα radiation and represented by diffraction angle 2θ angle, in which there are characteristic peaks at 2θ angles of 7.141, 7.787, 11.005, 14.215, 15.694, 16.169, 16.207, 17.536, 19.631, 20.545, 22.197, 23.946, 23.979, 24.952, 25.593, 25.640, 27.539, 27.636, 28.496, 29.719, 30.545, 31.742, 32.716, 35.040, 35.439 and 40.178.

In a preferred embodiment, the present invention provides crystal form H of the compound of formula (I), characterized in that: the crystal form H has an X-ray powder diffraction spectrum as shown in FIG. 5, which is obtained by using Cu-Kα radiation.

The present invention further provides a method for preparing the crystal form H of the compound of formula (I), comprising the steps of:

dissolving the compound of formula (I) in an appropriate amount of N,N-dimethylformamide to precipitate a crystal, and filtering the resulting crystal to obtain the desired crystal form H.

In another aspect, the present invention provides crystal form I of the compound of formula (I), characterized in that: the crystal form I has an X-ray powder diffraction spectrum, which is obtained by using Cu-Kα radiation and represented by diffraction angle 2θ angle, in which there are characteristic peaks at 2θ angles of 6.86, 10.44, 14.02, 21.19, 23.82, 24.73, 27.67, 28.37, 30.38, 30.41, 30.51, 32.05, 35.69, 36.28 and 41.55.

In another aspect, the present invention provides crystal form I of the compound of formula (I), characterized in that: the crystal form I has an X-ray powder diffraction spectrum, which is obtained by using Cu-Kα radiation and represented by diffraction angle 2θ angle, in which there are characteristic peaks at 2θ angles of 6.862, 10.441, 14.016, 21.185, 23.819, 24.733, 27.670, 28.371, 30.376, 30.409, 30.511, 32.050, 35.693, 36.281 and 41.553.

In a preferred embodiment, the present invention provides crystal form I of the compound of formula (I), characterized in that: the crystal form I has an X-ray powder diffraction spectrum as shown in FIG. 6, which is obtained by using Cu-Kα radiation.

The present invention further provides a method for preparing the crystal form I of the compound of formula (I), comprising the steps of:

dissolving the compound of formula (I) in an appropriate amount of ethyl acetate to precipitate a crystal, and filtering the resulting crystal to obtain the desired crystal form I.

The present invention further relates to a pharmaceutical composition comprising one or more of crystal forms A, B, C, D, H and I of the compound of formula (I) and one or more pharmaceutically acceptable carriers, diluents and excipients.

The present invention further relates to a pharmaceutical composition prepared by mixing one or more of crystal forms A, B, C, D, H and I of the compound of formula (I) of the present invention with one or more pharmaceutically acceptable carriers, diluents and excipients.

The present invention further relates to a method for preparing a pharmaceutical composition comprising the compound of formula (I) or a pharmaceutically acceptable salt thereof, comprising a step of mixing one or more of crystal forms A, B, C, D, H and I of the compound of formula (I) with one or more pharmaceutically acceptable carriers, diluents and excipients.

The pharmaceutical composition can be formulated into any one of pharmaceutically acceptable dosage forms. For example, the crystal form or the pharmaceutical formulation of the present invention can be formulated into a tablet, capsule, pill, granule, solution, suspension, syrup, injection (including injection solution, sterile powder for injection, and concentrated solution for injection), suppository, inhalant or spray.

The present invention further relates to a use of the crystal form A, B, C, D, H or I of the compound of formula (I) or the pharmaceutical composition of the present invention in the preparation of a medicament for treating a prolyl hydroxylase-mediated disease, such as anemia, by inhibting the prolyl hydroxylase.

The resulting crystal forms of the present invention are determined by X-ray powder diffraction spectrum (XRPD) and differential scanning calorimetry (DSC).

The crystallization method of the present invention is a conventional crystallization method, for example solvent volatilization crystallization, cooling crystallization and room temperature crystallization.

The starting material used in the method for preparing the crystal form of the present invention can be the compound of formula (I) in any form, and the specific forms include, but are not limited to, amorphous form, arbitrary crystal forms and the like.

In the specification and claims of the present application, unless otherwise indicated, the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "slurrying" used in the present invention refers to a purification method which utilizes the property that the solubility of a compound is poor in a solvent, while the solubility of impurities is good in the solvent. Slurrying purification can remove color, change crystal form or remove small amounts of impurities.

The term "X-ray powder diffraction spectrum" or "XRPD" used in the present invention refers to an X-ray powder diffraction spectrum that is obtained according to the Bragg formula 2d sin θ=nλ (where λ is the wavelength of the X-ray, λ=1.54056 Å, the order of diffraction n is any positive integer, generally taking the first-order diffraction peak, n=1), when the X-ray is incident on a certain atomic plane of a crystal or a partial crystal sample having a d-lattice plane spacing at a glancing angle θ (the complementary angle of incidence angle, also called the Bragg angle), the Bragg equation can be satisfied.

The term "differential scanning calorimetry" or "DSC" used in the present invention means to measure the temperature difference and heat flow difference between the sample and the reference during the heating or constant temperature process of the sample, to characterize all physical and chemical changes associated with the thermal effect, and to obtain phase change information of the sample.

The term "2θ" or "2θ angle" used in the present invention refers to the diffraction angle, θ is the Bragg angle, and the unit of which is ° or degree. The error range of 2θ is ±0.3 or ±0.2 or ±0.1.

The term "interplanar spacing" or "interplanar distance (d value)" used in the present invention means that the space lattice selects three unparallel unit vectors a, b, c, wherein each of them connects two adjacent lattice dots, and the three vectors divide the lattice into juxtaposed parallelepiped units, called the interplanar spacing. The space lattice is divided according to the determined parallelepiped unit lines to obtain a set of linear grids, which is called a space lattice or a lattice. The lattice reflects the periodicity of the crystal structure with geometric points and lines. Different crystal planes have different interplanar spacings (i.e., distance between two adjacent parallel crystal planes); the unit is Å or angstrom.

Advantageous Effects of the Present Invention

The crystal forms A, B, C, D, H and I of the compound of formula (I) prepared according to the present invention have high purity, and are stable under the conditions of lighting, high temperature and high humidity. The HPLC purity change is slight, and the chemical stability is high. The crystal forms A, B, C, D, H and I of the compound of formula (I) prepared according to the present invention can meet the production, transportation and storage requirements of drug products. Their preparation processes are stable, repeatable and controllable, and can be adapted to industrial production.

DETAILED DESCRIPTION OF THE INVENTION

The present invention will be illustrated by the following examples in detail. The examples of the present invention are merely intended to describe the technical solution of the present invention, and should not be considered as limiting the spirit and scope of the present invention.

Test conditions for the instruments used in the experiments:

1. Differential Scanning calorimeter, DSC
Instrument type: MettlerToledo DSC 3+STAR$^e$ System
Purging gas: Nitrogen
Heating rate: 10.0° C./min
Temperature range: 40-300° C.
2. X-ray Powder Diffraction, XRPD
Instrument type: Bruker D8 Discover A25 X-ray powder diffractometer
Ray: monochromatic Cu-Kα ray (λ=1.5406)
Scanning mode: θ/2θ, Scanning range: 2-40°
Voltage: 40 kV, Electric current: 40 mA
3. Dynamic Vapour Sorption, DVS
Instrument type: DVS advantage
Temperature: 25° C.
Solvent: water
Humidity change: 0-95-0-95-0% RH, dm/dt=0.002

Example 1

Figure 1:
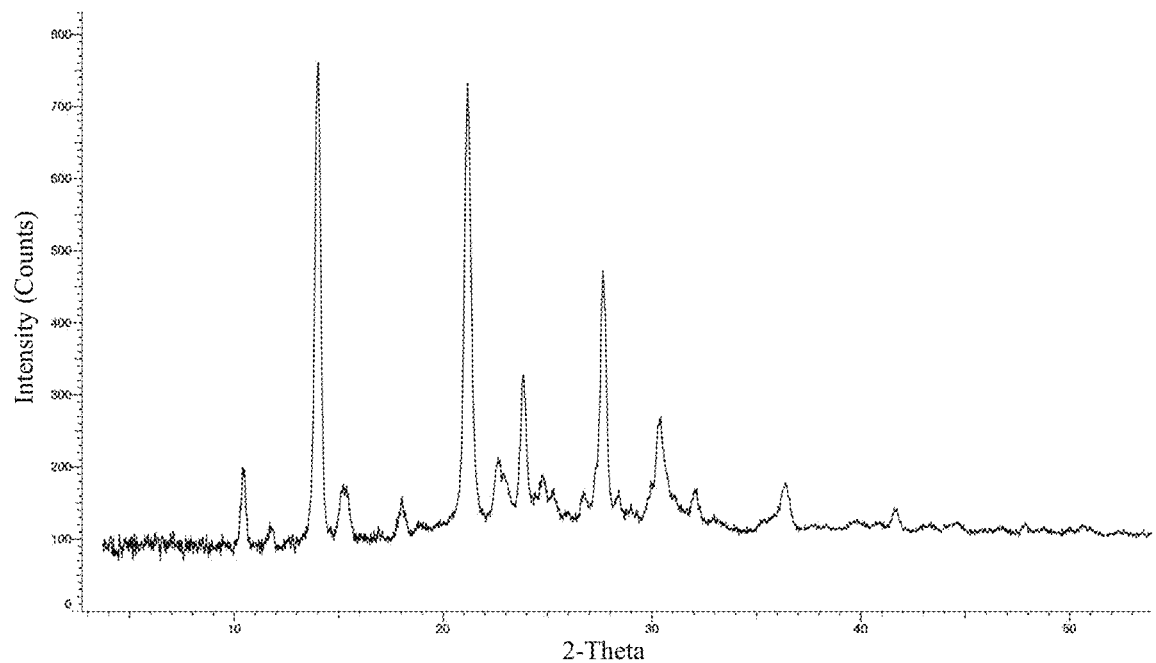
FIG. 1 shows the XRPD spectrum of crystal form A of the compound of formula (I).
Figure 7:
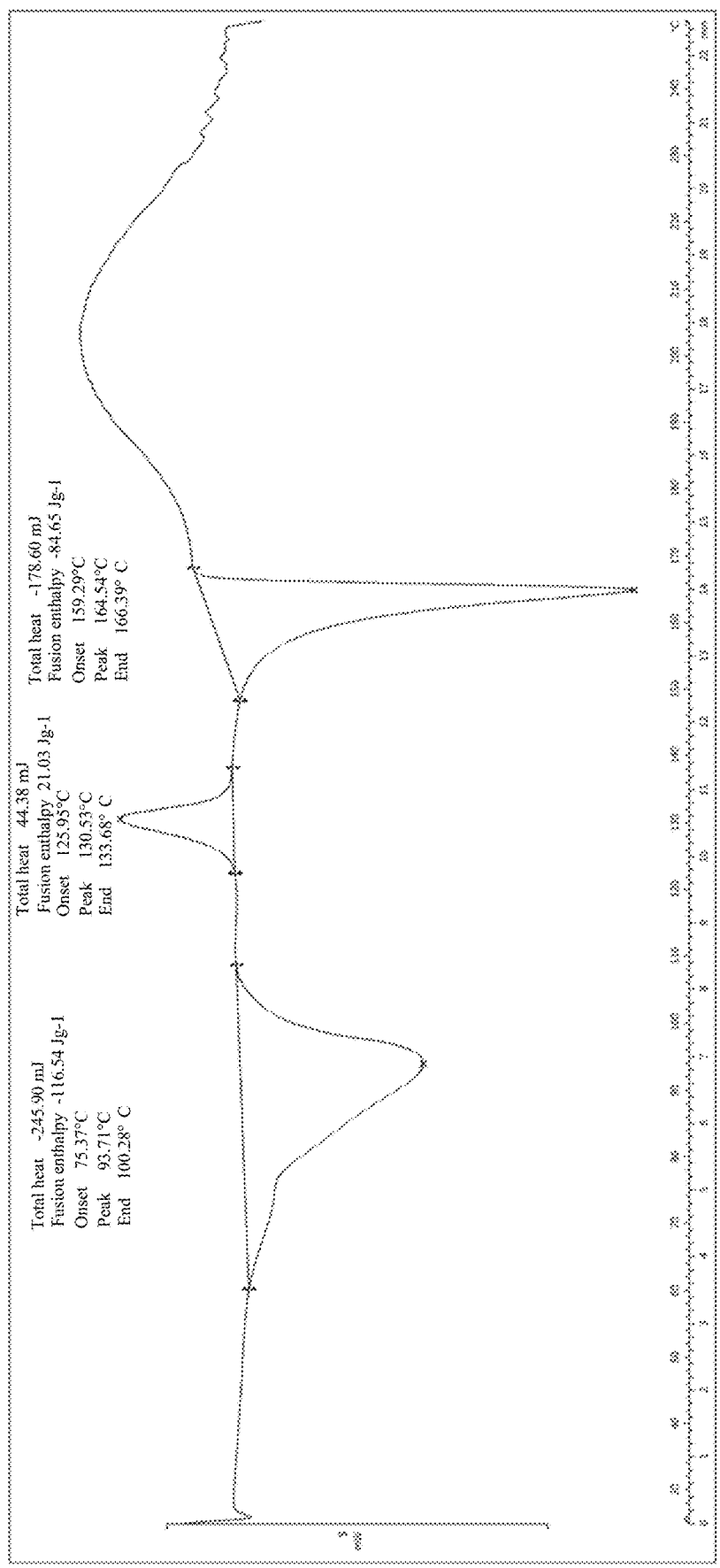
FIG. 7 shows the DSC spectrum of crystal form A of the compound of formula (I).

10 mg of the compound of formula (I) (prepared according to the method disclosed in WO2017059623) was added to a reaction flask, and dissolved in 5 ml of dimethyl sulfoxide. The solution was left to stand at room temperature, and volatilized to dryness to obtain about 9 mg of a pale yellow solid. The X-ray diffraction spectrum of the crystal sample is shown in FIG. 1, and the DSC spectrum of the crystal sample is shown in FIG. 7. The crystal form was defined as crystal form A, and the characteristic peak positions are shown in the following table:

TABLE 1

Characteristic peaks of crystal form A

| Peak No. | 2θ[°] | d[Å] | I[%] |
|---|---|---|---|
| Peak 1 | 10.444 | 8.46326 | 16.3 |
| Peak 2 | 11.782 | 7.50510 | 3.8 |
| Peak 3 | 14.008 | 6.31697 | 100 |
| Peak 4 | 15.268 | 5.79850 | 9.8 |
| Peak 5 | 18.034 | 4.91495 | 7.1 |
| Peak 6 | 21.183 | 4.19092 | 91.1 |
| Peak 7 | 22.656 | 3.92156 | 10.2 |
| Peak 8 | 22.958 | 3.87073 | 6.3 |
| Peak 9 | 23.849 | 3.72809 | 27.8 |
| Peak 10 | 24.775 | 3.59071 | 6.9 |
| Peak 11 | 25.291 | 3.51865 | 4.5 |
| Peak 12 | 26.760 | 3.32871 | 3.8 |
| Peak 13 | 27.675 | 3.22078 | 49.7 |
| Peak 14 | 28.359 | 3.14458 | 2.8 |
| Peak 15 | 30.372 | 2.94061 | 19.0 |

TABLE 1-continued

Characteristic peaks of crystal form A

| Peak No. | 2θ[°] | d[Å] | I[%] |
|---|---|---|---|
| Peak 16 | 32.074 | 2.78836 | 4.8 |
| Peak 17 | 36.379 | 2.46765 | 8.1 |
| Peak 18 | 41.668 | 2.16582 | 2.8 |

Example 2

Figure 2:
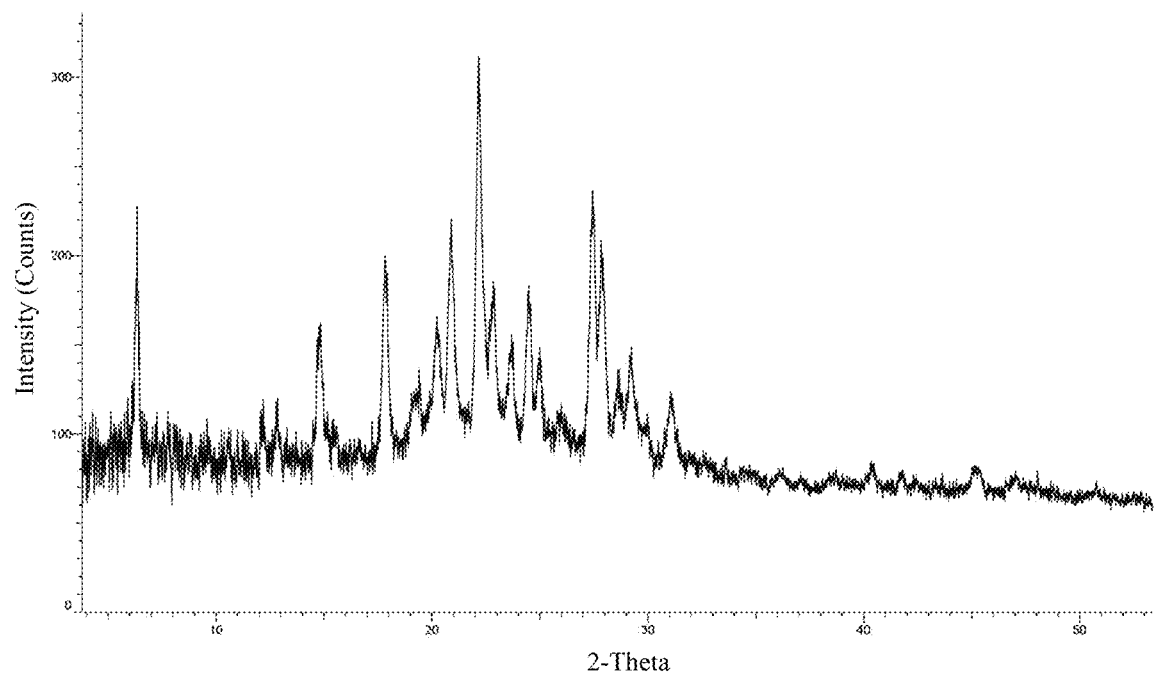
FIG. 2 shows the XRPD spectrum of crystal form B of the compound of formula (I).
Figure 8:
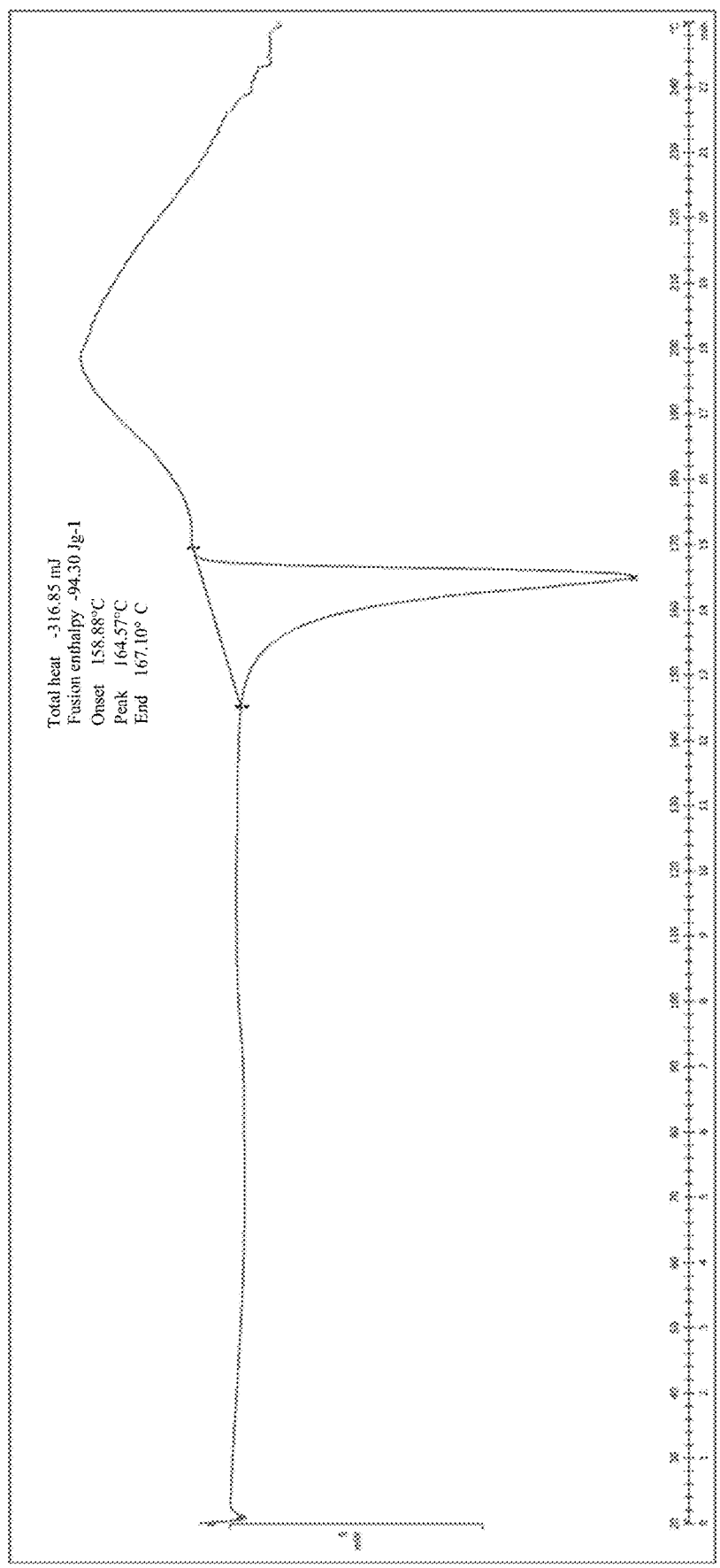
FIG. 8 shows the DSC spectrum of crystal form B of the compound of formula (I).

10 mg of the compound of formula (I) was added to a reaction flask, and 5 ml of dichloromethane was added. The mixture was slurried respectively at room temperature and 50° C. for three days, filtrated and dried under vacuum at 40° C. for two hours. About 8 mg of a pale yellow solid were obtained under both conditions. The X-ray diffraction spectra of the two crystal samples are the same. The X-ray diffraction spectrum of the crystal sample is shown in FIG. 2, and the DSC spectrum of the crystal sample is shown in FIG. 8. The crystal form was defined as crystal form B, and the characteristic peak positions are shown in the following table:

TABLE 2

Characteristic peaks of crystal form B

| Peak No. | 2θ[°] | d[Å] | I[%] |
|---|---|---|---|
| Peak 1 | 6.341 | 13.92834 | 64.6 |
| Peak 2 | 12.165 | 7.26976 | 12.2 |
| Peak 3 | 12.836 | 6.89095 | 15.8 |
| Peak 4 | 14.747 | 6.00237 | 31.0 |
| Peak 5 | 17.840 | 4.96793 | 51.9 |
| Peak 6 | 19.345 | 4.58467 | 11.1 |
| Peak 7 | 20.273 | 4.37691 | 23.6 |
| Peak 8 | 20.894 | 4.24812 | 55.7 |
| Peak 9 | 22.172 | 4.00605 | 100 |
| Peak 10 | 22.852 | 3.88846 | 36.2 |
| Peak 11 | 23.675 | 3.75503 | 19.4 |
| Peak 12 | 24.490 | 3.63189 | 36.2 |
| Peak 13 | 25.033 | 3.55440 | 13.9 |
| Peak 14 | 26.001 | 3.42421 | 6.3 |
| Peak 15 | 27.457 | 3.24584 | 70.5 |
| Peak 16 | 27.856 | 3.20019 | 53.7 |
| Peak 17 | 28.542 | 3.12484 | 14.8 |
| Peak 18 | 29.187 | 3.05720 | 24.6 |
| Peak 19 | 29.994 | 2.97678 | 10.9 |
| Peak 20 | 31.124 | 2.87128 | 16.1 |
| Peak 21 | 32.616 | 2.74322 | 1.0 |
| Peak 22 | 40.361 | 2.23289 | 2.8 |

Example 3

Figure 3:
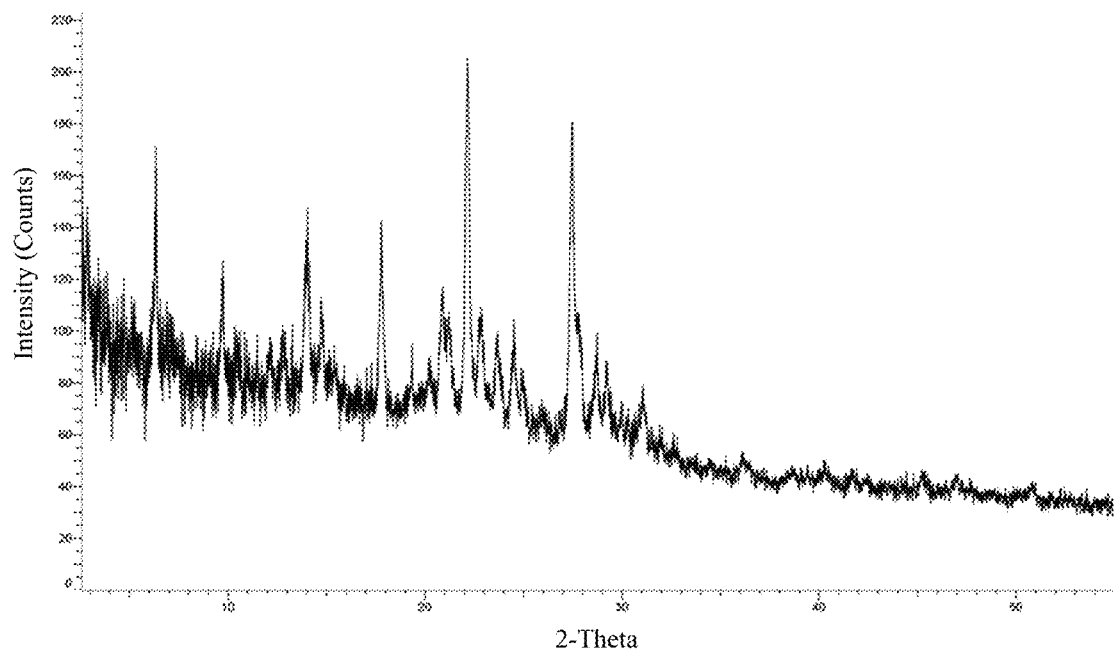
FIG. 3 shows the XRPD spectrum of crystal form C of the compound of formula (I).
Figure 9:
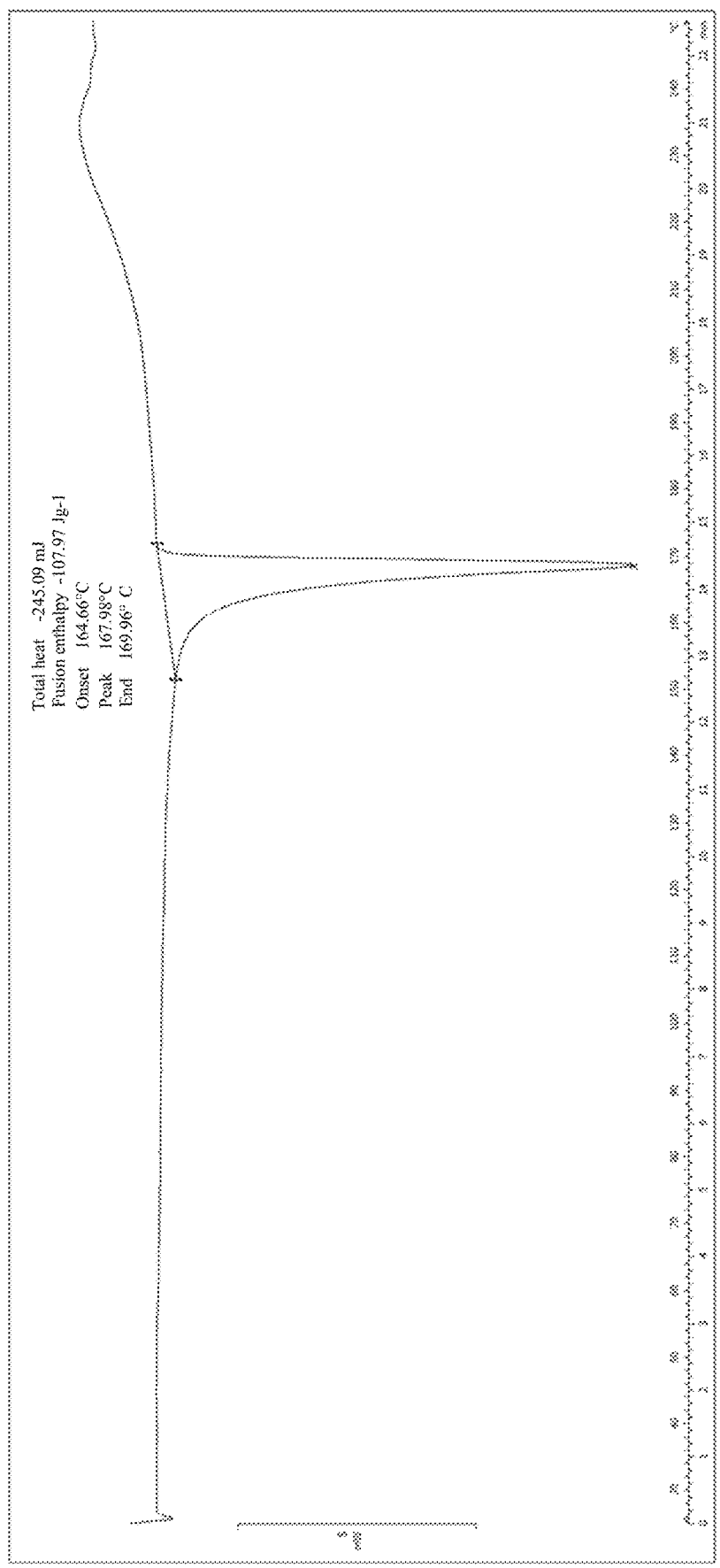
FIG. 9 shows the DSC spectrum of crystal form C of the compound of formula (I).

80 mg of the compound of formula (I) was added to a reaction flask, and dissolved in 40 ml of a mixed solvent of methanol/water ($V_{water}:V_{methanol}$=1:9) under stirring. The solution was left to stand at room temperature, and volatilized to dryness to obtain about 75 mg of a pale yellow solid. The X-ray diffraction spectrum of the crystal sample is shown in FIG. 3, and the DSC spectrum of the crystal sample is shown in FIG. 9. The crystal form was defined as crystal form C, and the characteristic peak positions are shown in the following table:

TABLE 3

Characteristic peaks of crystal form C

| Peak No. | 2θ[°] | d[Å] | I[%] |
|---|---|---|---|
| Peak 1 | 6.333 | 13.94621 | 66.2 |
| Peak 2 | 9.713 | 9.09827 | 36.2 |
| Peak 3 | 14.040 | 6.30263 | 56.6 |
| Peak 4 | 14.703 | 6.02019 | 28.7 |
| Peak 5 | 17.791 | 4.98149 | 57.2 |
| Peak 6 | 19.347 | 4.58422 | 11.4 |
| Peak 7 | 20.222 | 4.38786 | 5.4 |
| Peak 8 | 20.840 | 4.25909 | 28.0 |
| Peak 9 | 21.193 | 4.18890 | 22.8 |
| Peak 10 | 22.163 | 4.00769 | 100 |
| Peak 11 | 22.847 | 3.88929 | 21.8 |
| Peak 12 | 23.678 | 3.75454 | 21.9 |
| Peak 13 | 24.527 | 3.62648 | 28.2 |
| Peak 14 | 24.926 | 3.56939 | 10.6 |
| Peak 15 | 27.472 | 3.24407 | 87.8 |
| Peak 16 | 28.727 | 3.10511 | 25.7 |
| Peak 17 | 29.232 | 3.05264 | 19.2 |
| Peak 18 | 31.060 | 2.87701 | 14.1 |

Example 4

Figure 4:
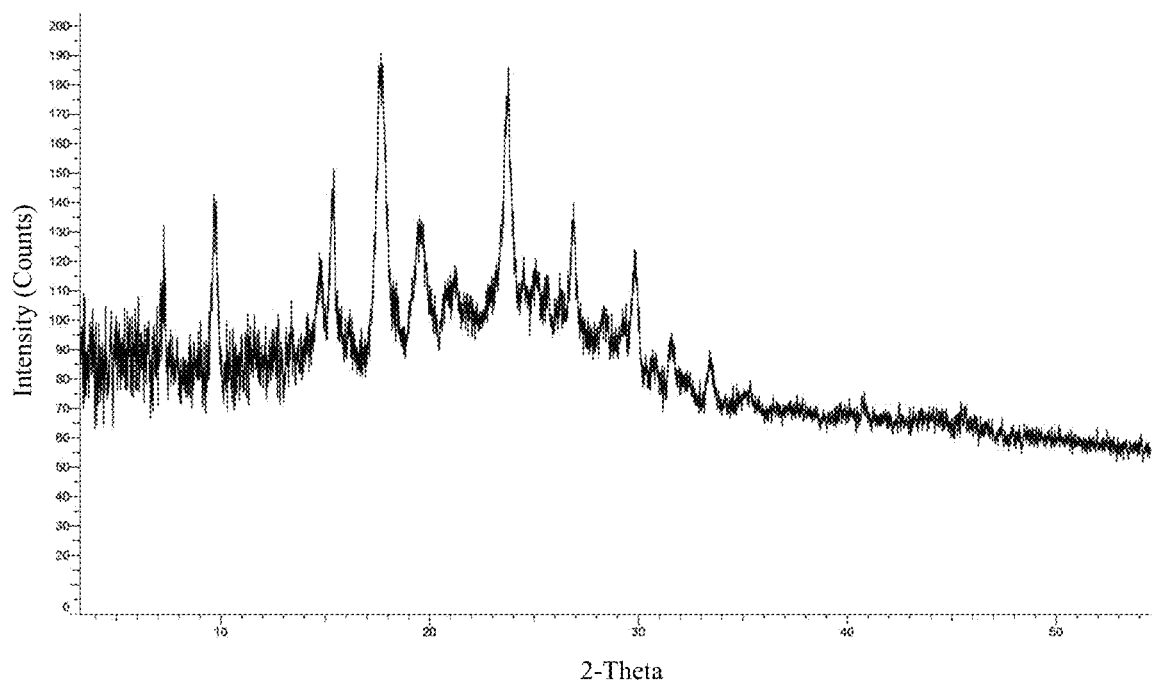
FIG. 4 shows the XRPD spectrum of crystal form D of the compound of formula (I).
Figure 10:
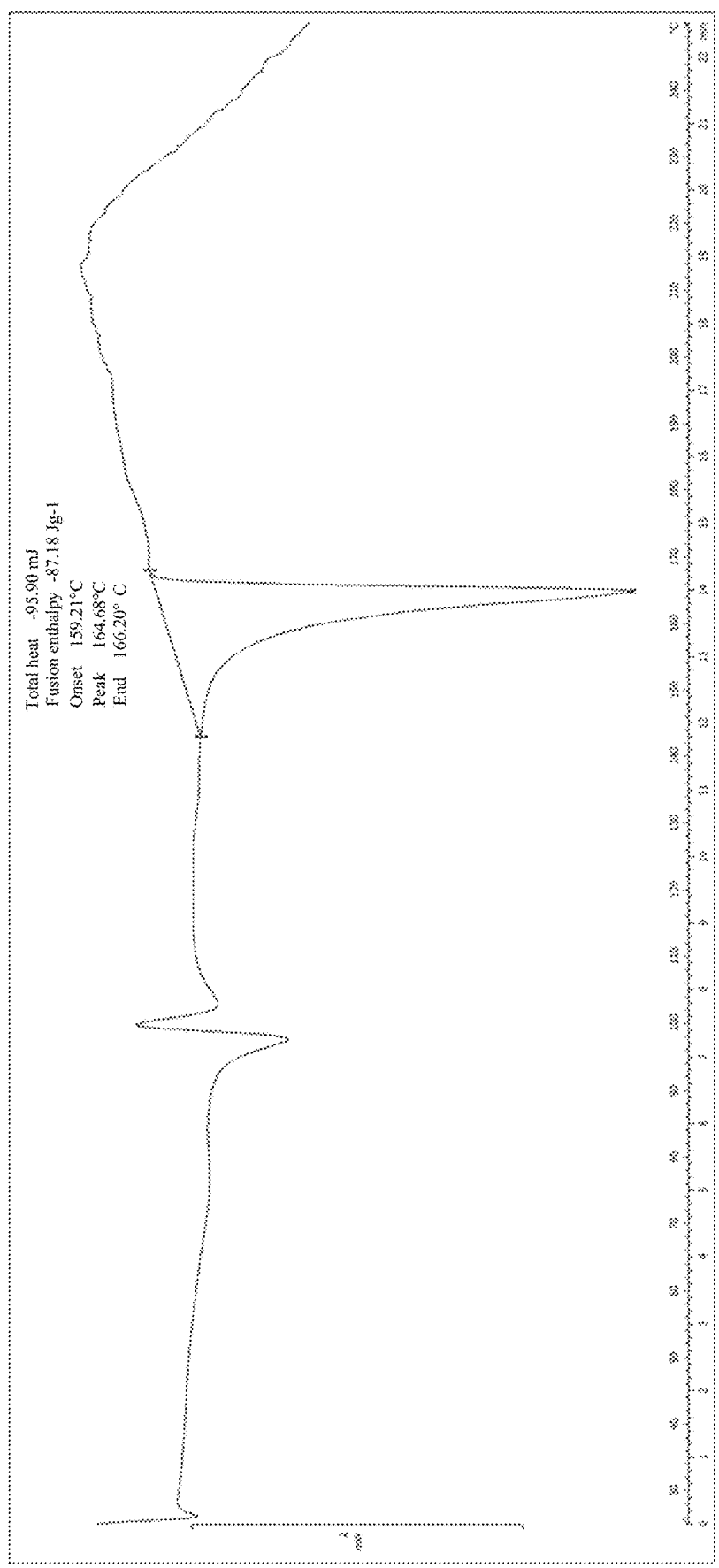
FIG. 10 shows the DSC spectrum of crystal form D of the compound of formula (I).

80 mg of the compound of formula (I) was added to a reaction flask, and dissolved in 40 ml of 1,4-dioxane under stirring. The solution was left to stand at room temperature, and volatilized to dryness to obtain about 75 mg of a pale yellow solid. The X-ray diffraction spectrum of the crystal sample is shown in FIG. 4, and the DSC spectrum of the crystal sample is shown in FIG. 10. The crystal form was defined as crystal form D, and the characteristic peak positions are shown in the following table:

TABLE 4

Characteristic peaks of crystal form D

| Peak No. | 2θ[°] | d[Å] | I[%] |
|---|---|---|---|
| Peak 1 | 7.281 | 12.13196 | 57.5 |
| Peak 2 | 9.673 | 9.13592 | 66.8 |
| Peak 3 | 9.724 | 9.08861 | 51.6 |
| Peak 4 | 9.794 | 9.02332 | 61.7 |
| Peak 5 | 14.723 | 6.01170 | 33.7 |
| Peak 6 | 15.369 | 5.76054 | 46.4 |
| Peak 7 | 17.665 | 5.01666 | 100 |
| Peak 8 | 19.556 | 4.53566 | 31.1 |
| Peak 9 | 20.756 | 4.27609 | 9.5 |
| Peak 10 | 21.207 | 4.18608 | 17.5 |
| Peak 11 | 23.785 | 3.73802 | 82.9 |
| Peak 12 | 25.125 | 3.54154 | 8.1 |
| Peak 13 | 26.247 | 3.39269 | 1.6 |
| Peak 14 | 26.882 | 3.31390 | 32.4 |
| Peak 15 | 28.326 | 3.14817 | −1.3 |
| Peak 16 | 28.360 | 3.14444 | 8.8 |
| Peak 17 | 29.853 | 2.99052 | 32.8 |
| Peak 18 | 31.578 | 2.83097 | 15.6 |
| Peak 19 | 33.425 | 2.67864 | 13.3 |
| Peak 20 | 35.377 | 2.53520 | 4.0 |

Example 5

Figure 5:
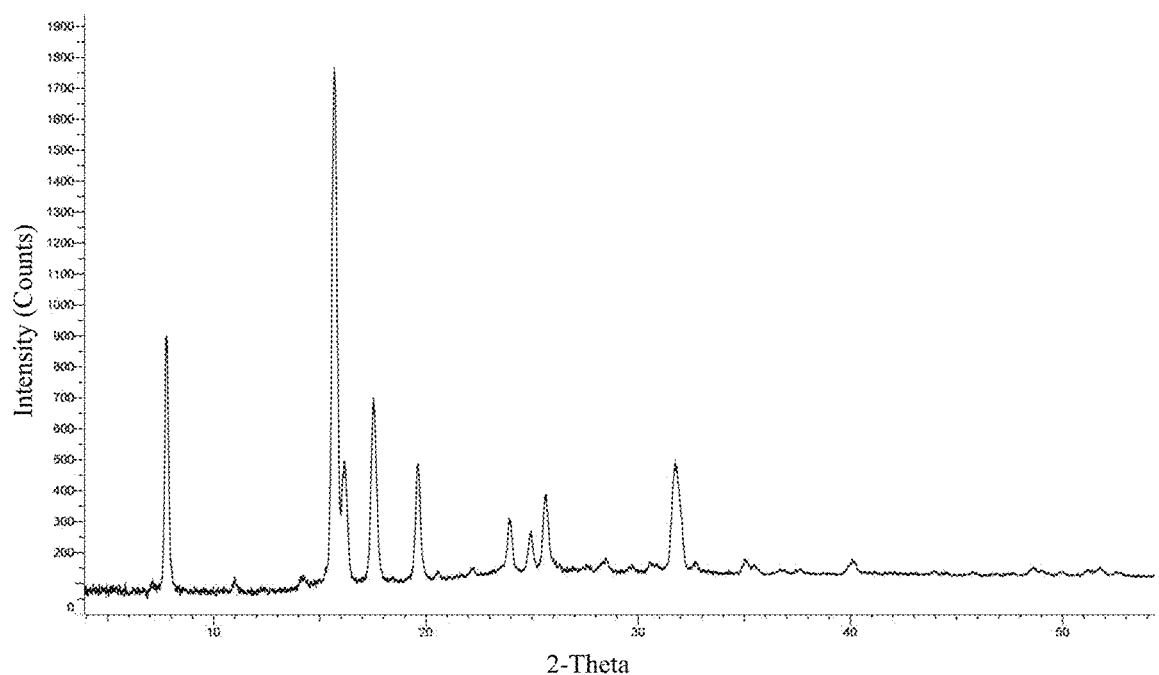
FIG. 5 shows the XRPD spectrum of crystal form H of the compound of formula (I).
Figure 11:
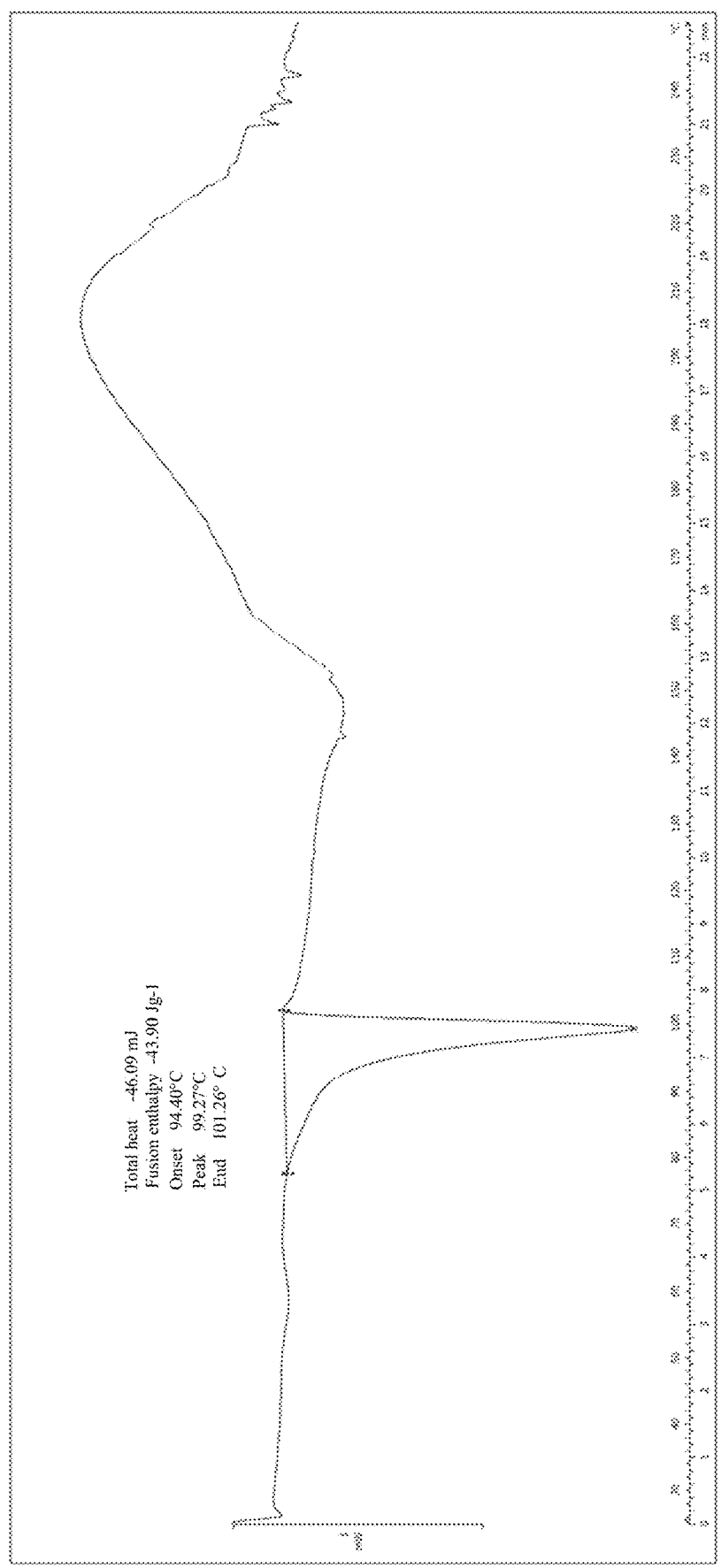
FIG. 11 shows the DSC spectrum of crystal form H of the compound of formula (I).

80 mg of the compound of formula (I) was added to a reaction flask, and dissolved in 40 ml of N,N-dimethylformamide under stirring. The solution was left to stand at room temperature, and volatilized to dryness to obtain about 78 mg of a pale yellow solid. The X-ray diffraction spectrum of the crystal sample is shown in FIG. 5, and the DSC spectrum of the crystal sample is shown in FIG. 11. The crystal form was defined as crystal form H, and the characteristic peak positions are shown in the following table:

TABLE 5

Characteristic peaks of crystal form H

| Peak No. | 2θ[°] | d[Å] | I[%] |
|---|---|---|---|
| Peak 1 | 7.141 | 12.36821 | 3.1 |
| Peak 2 | 7.787 | 11.34440 | 48.9 |
| Peak 3 | 11.005 | 8.03351 | 3.1 |
| Peak 4 | 14.215 | 6.22537 | 1.1 |
| Peak 5 | 15.694 | 5.64204 | 100 |
| Peak 6 | 16.169 | 5.47734 | 22.9 |
| Peak 7 | 16.207 | 5.46477 | 21.8 |
| Peak 8 | 17.536 | 5.05333 | 35.3 |
| Peak 9 | 19.631 | 4.51844 | 22.1 |
| Peak 10 | 20.545 | 4.31942 | 0.8 |
| Peak 11 | 22.197 | 4.00167 | 1.2 |
| Peak 12 | 23.946 | 3.71315 | 9.4 |
| Peak 13 | 23.979 | 3.70820 | 8.7 |
| Peak 14 | 24.952 | 3.56572 | 6.6 |
| Peak 15 | 25.593 | 3.47777 | 12.4 |
| Peak 16 | 25.640 | 3.47154 | 13.7 |
| Peak 17 | 27.539 | 3.23637 | −0.1 |
| Peak 18 | 27.636 | 3.22515 | 0.4 |
| Peak 19 | 28.496 | 3.12976 | 2.5 |
| Peak 20 | 29.719 | 3.00367 | 0.6 |
| Peak 21 | 30.545 | 2.92433 | 1.3 |
| Peak 22 | 31.742 | 2.81672 | 20.2 |
| Peak 23 | 32.716 | 2.73505 | 1.0 |
| Peak 24 | 35.040 | 2.55879 | 2.0 |
| Peak 25 | 35.439 | 2.53090 | 1.1 |
| Peak 26 | 40.178 | 2.24266 | 1.7 |

Example 6

Figure 6:
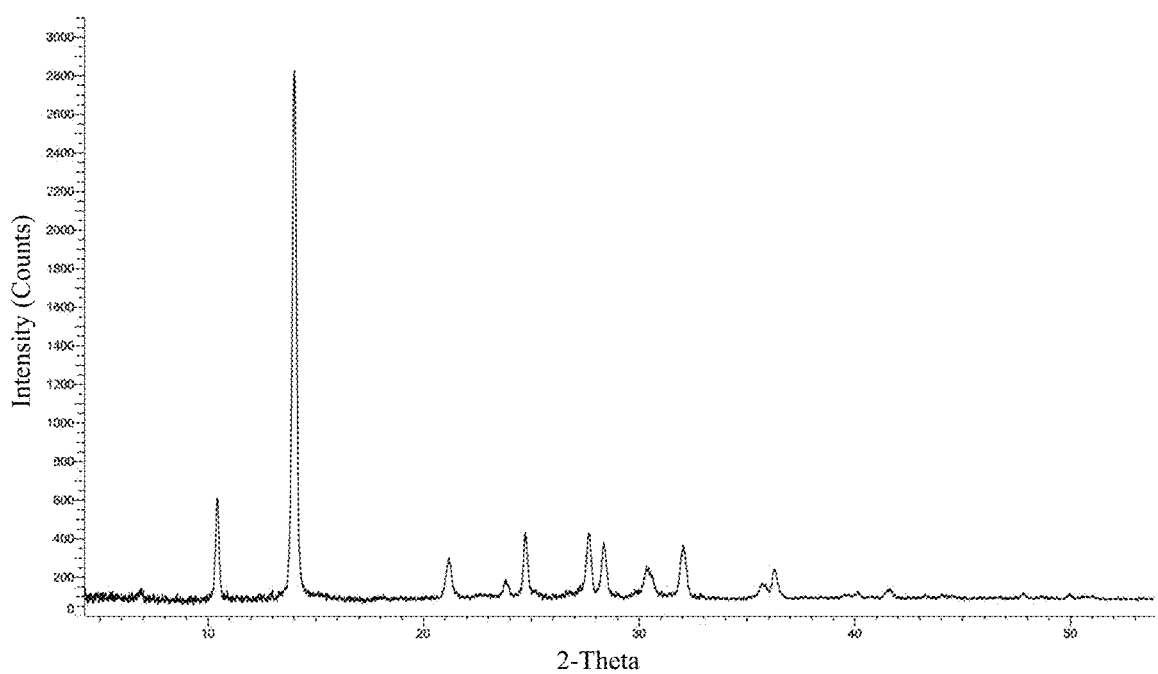
FIG. 6 shows the XRPD spectrum of crystal form I of the compound of formula (I).
Figure 12:
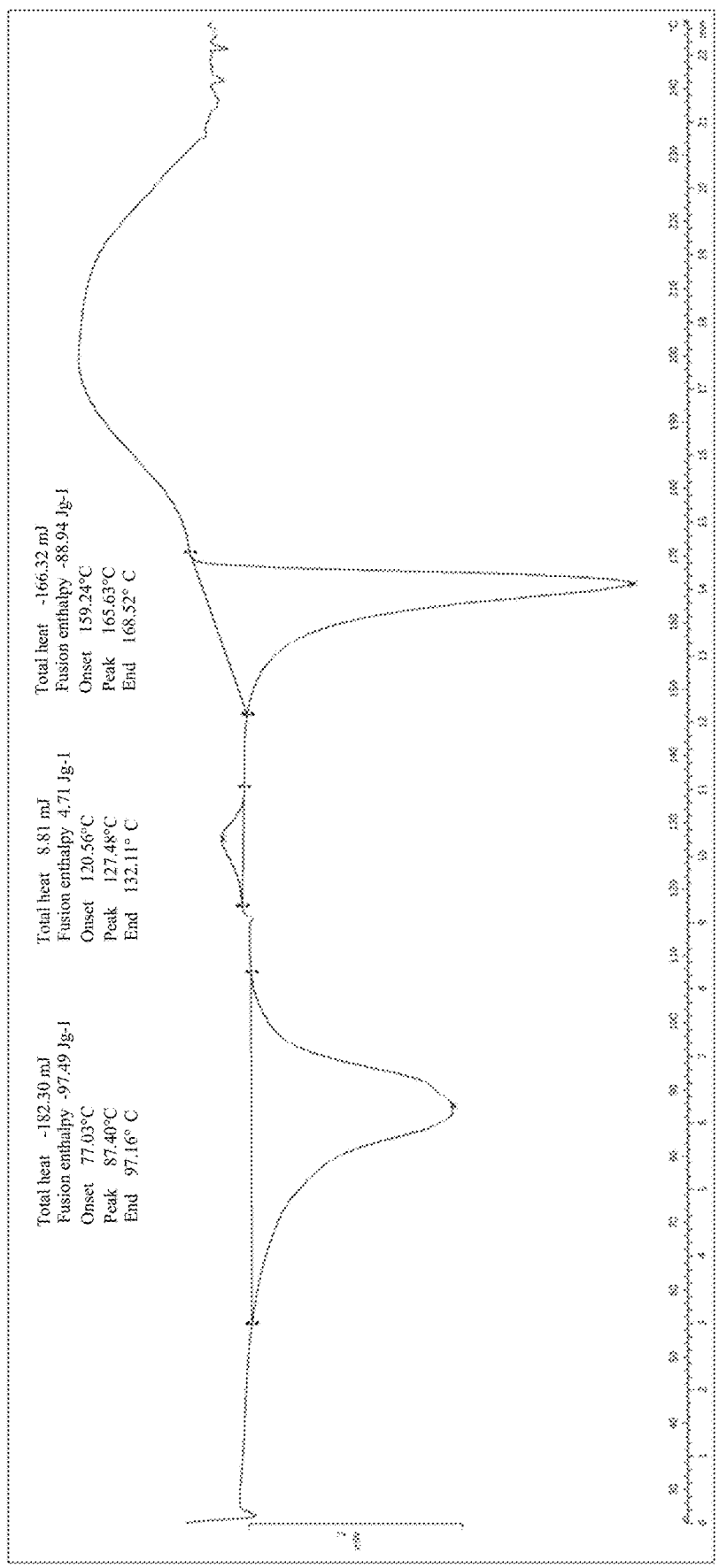
FIG. 12 shows the DSC spectrum of crystal form I of the compound of formula (I).

80 mg of the compound of formula (I) was added to a reaction flask, and dissolved in 40 ml of ethyl acetate under stirring. The solution was left to stand at room temperature, and volatilized to dryness to obtain about 75 mg of a pale yellow solid. The X-ray diffraction spectrum of the crystal sample is shown in FIG. 6, and the DSC spectrum of the crystal sample is shown in FIG. 12. The crystal form was defined as crystal form I, and the characteristic peak positions are shown in the following table:

TABLE 6

Characteristic peaks of crystal form I

| Peak No. | 2θ[°] | d[Å] | I[%] |
|---|---|---|---|
| Peak 1 | 6.862 | 12.87079 | 2.1 |
| Peak 2 | 10.441 | 8.46607 | 19.5 |
| Peak 3 | 14.016 | 6.31374 | 100 |
| Peak 4 | 21.185 | 4.19048 | 7.1 |
| Peak 5 | 23.819 | 3.73263 | 3.1 |
| Peak 6 | 24.733 | 3.59677 | 11.5 |
| Peak 7 | 27.670 | 3.22134 | 11.8 |
| Peak 8 | 28.371 | 3.14330 | 10.0 |
| Peak 9 | 30.376 | 2.94026 | 4.9 |
| Peak 10 | 30.409 | 2.93711 | 5.1 |
| Peak 11 | 30.511 | 2.92755 | 4.6 |
| Peak 12 | 32.050 | 2.79033 | 9.3 |
| Peak 13 | 35.693 | 2.51348 | 2.6 |
| Peak 14 | 36.281 | 2.47411 | 5.4 |
| Peak 15 | 41.553 | 2.17155 | 1.4 |

Example 7

Physical stability test was carried out on the samples of crystal forms A, B, C, D, H and I under different placement conditions. The placement conditions were:

1. 40° C., humidity 75%, open/sealed;
2. 25° C., humidity 60%, open; and
3. 2-6° C., sealed.

The test results are shown in Table 7.

TABLE 7

Physical stability of each crystal form

| Day 0 | | Physical stability (XRPD) Crystal form | | | | | |
|---|---|---|---|---|---|---|---|
| | | A | B | C | D | I | H |
| 1 week | 40° C. open | ✓ | ✓ | x | x | ✓ | x |
| | 40° C. sealed | ✓ | ✓ | x | x | ✓ | ✓ |
| | 25° C. open | ✓ | ✓ | x | x | ✓ | ✓ |
| | 4° C. sealed | ✓ | ✓ | x | x | ✓ | ✓ |
| 2 weeks | 40° C. open | ✓ | ✓ | / | / | ✓ | / |
| | 40° C. sealed | ✓ | ✓ | / | / | ✓ | / |
| | 25° C. open | ✓ | ✓ | / | / | ✓ | / |
| | 4° C. sealed | ✓ | ✓ | / | / | ✓ | / |
| 1 month | 40° C. open | ✓ | ✓ | / | / | ✓ | / |
| | 40° C. sealed | ✓ | ✓ | / | / | ✓ | / |
| | 25° C. open | ✓ | ✓ | / | / | ✓ | / |
| | 4° C. sealed | ✓ | ✓ | / | / | ✓ | / |

Note:
✓ means that the crystal form did not change; x means that the crystal form changed; and / means that the crystal form was not determined.

It can be seen from the table that crystal forms C, D and H changed after one week, indicating that crystal forms C, D and H have a poor physical stability; crystal forms A, B and I did not change after one month, indicating that crystal forms A, B and I have a good physical stability.

Example 8

Figure 13:
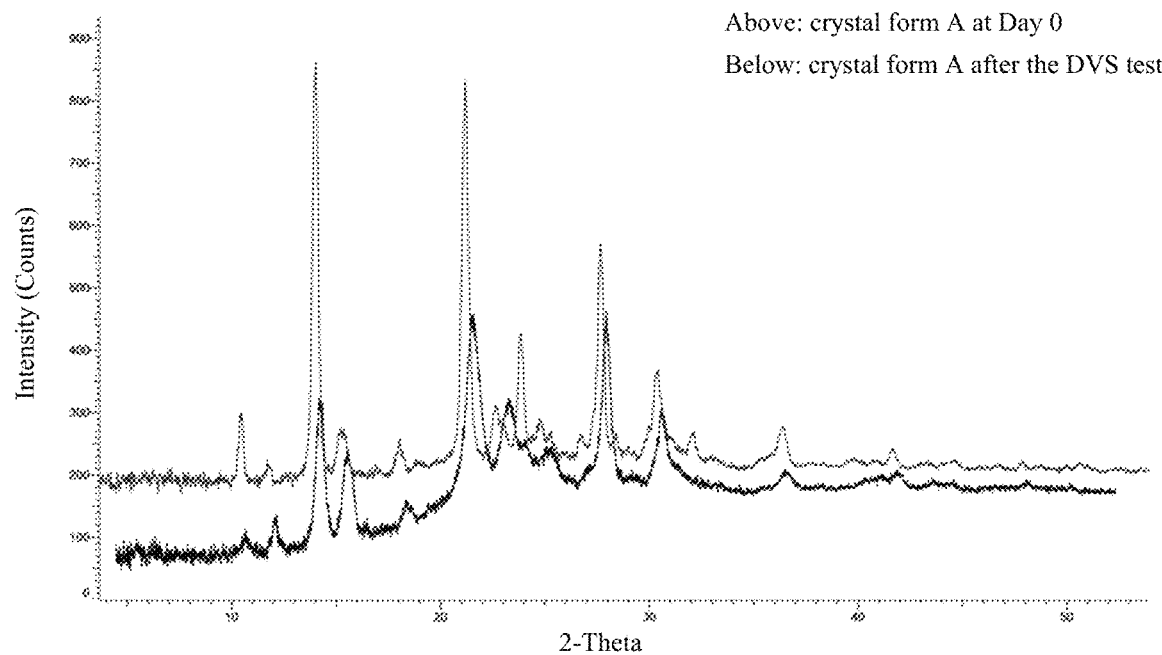
FIG. 13 shows the comparative XRPD spectrum of crystal form A of the compound of formula (I) before and after the DVS test.
Figure 14:
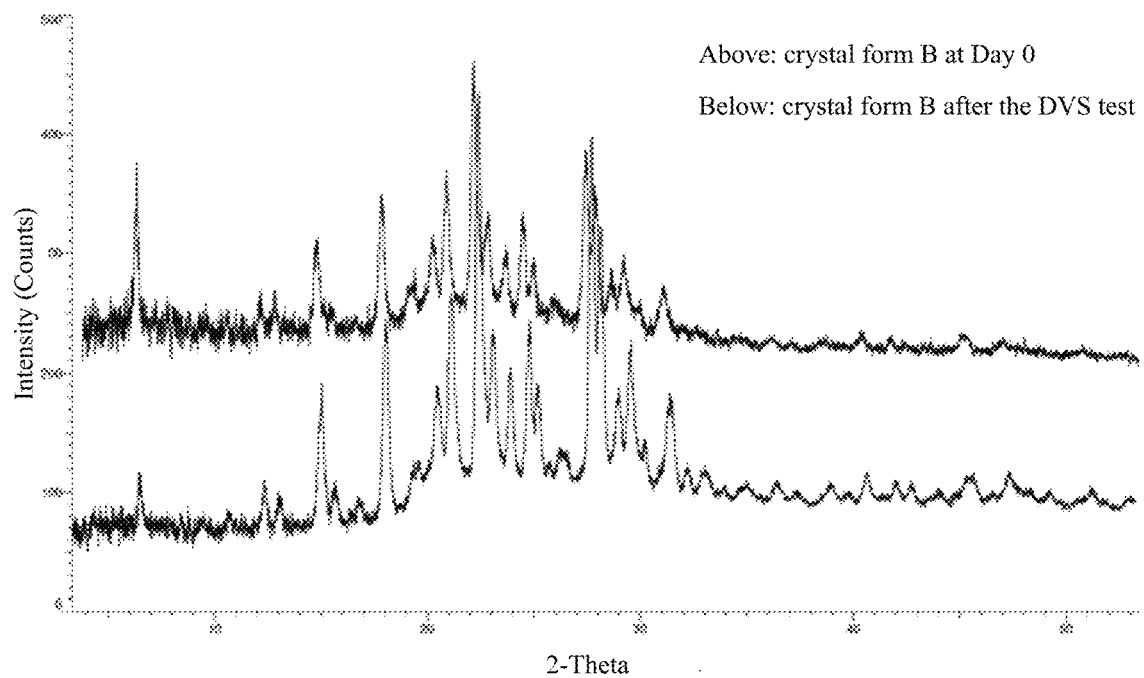
FIG. 14 shows the comparative XRPD spectrum of crystal form B of the compound of formula (I) before and after the DVS test.
Figure 15:
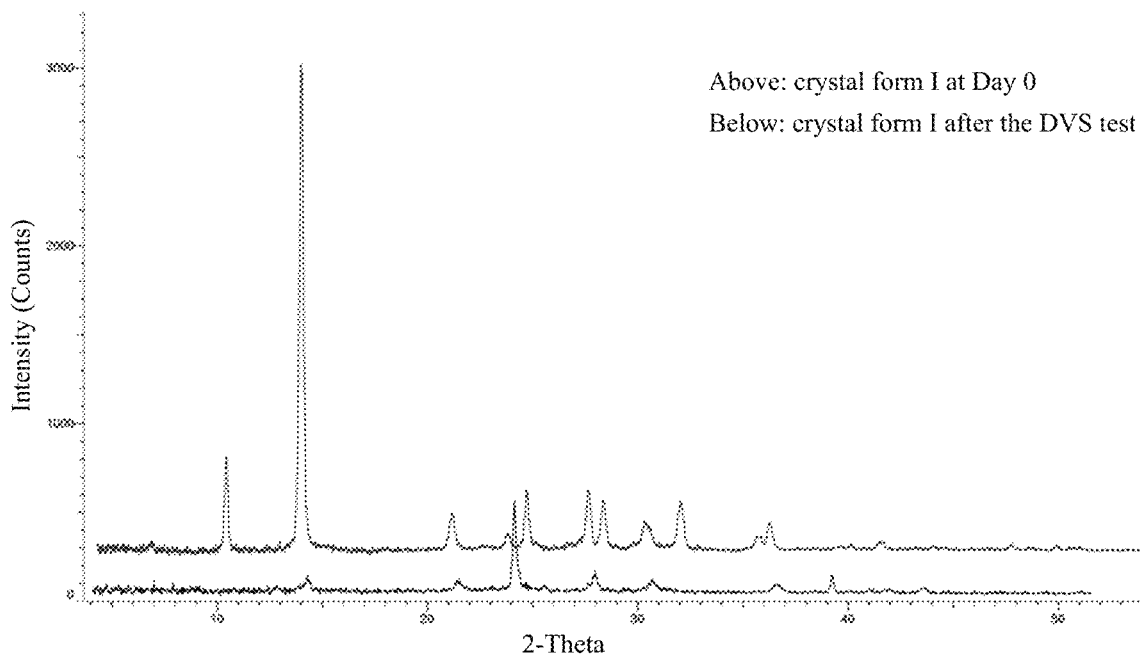
FIG. 15 shows the comparative XRPD spectrum of crystal form I of the compound of formula (I) before and after the DVS test.
Figure 16:
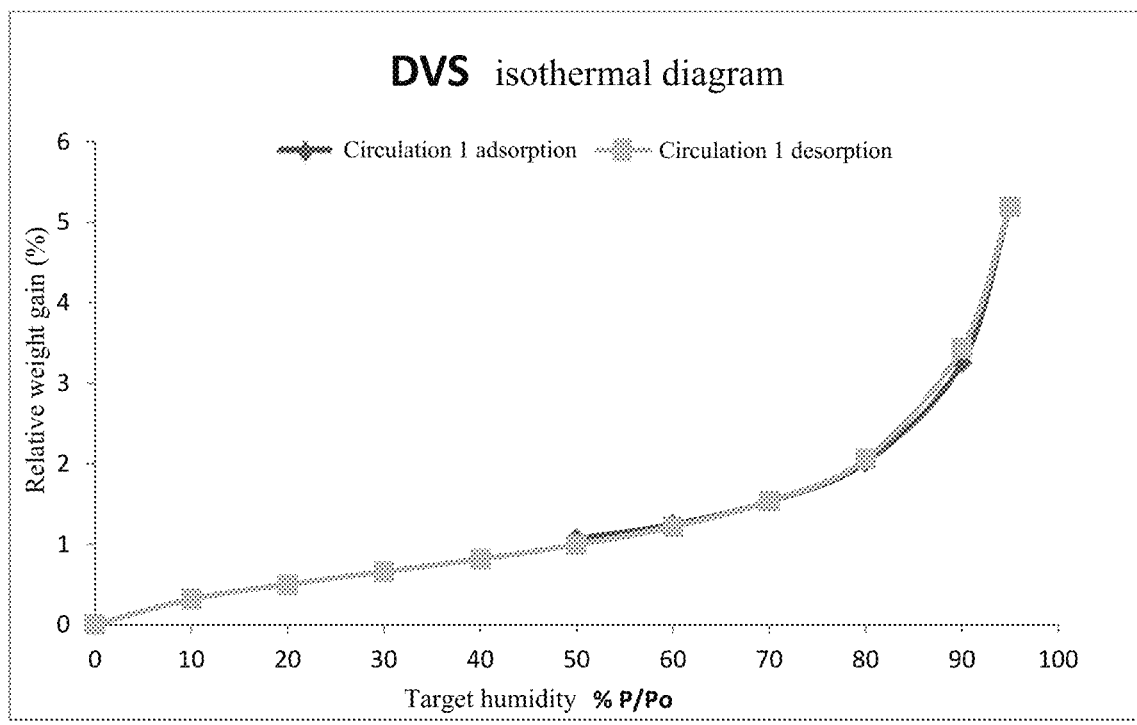
FIG. 16 shows the DVS circulation 1 diagram of crystal form B of the compound of formula (I).
Figure 17:
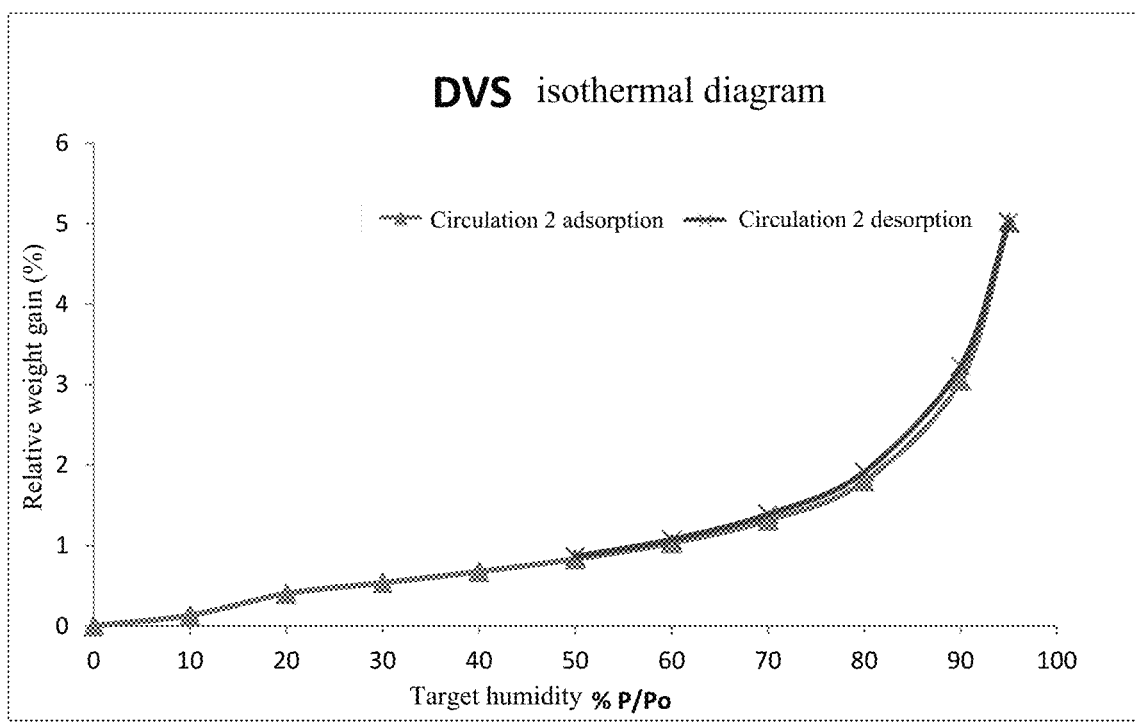
FIG. 17 shows the DVS circulation 2 diagram of crystal form B of the compound of formula (I).

XRPD test was carried out on the samples of crystal forms A, B and I after the DVS test, and the XRPD results of each crystal form before and after the DVS test were compared. The comparative XRPD spectra of each crystal form are shown in FIGS. 13-15.

DVS instrument parameters:
Temperature: 25° C.
Solvent: water
Humidity change: 50%-95%-0%-95%-50% RH, dm/dt=0.002
Maximum step size: 360 minutes The XRPD results showed that crystal form B did not change before and after the DVS test; crystal form A did not change, but the crystallinity thereof decreased; and crystal form I changed. Therefore, crystal form I is the most sensitive to humidity, while crystal form B is the most stable to humidity.

Example 9

Figure 18:
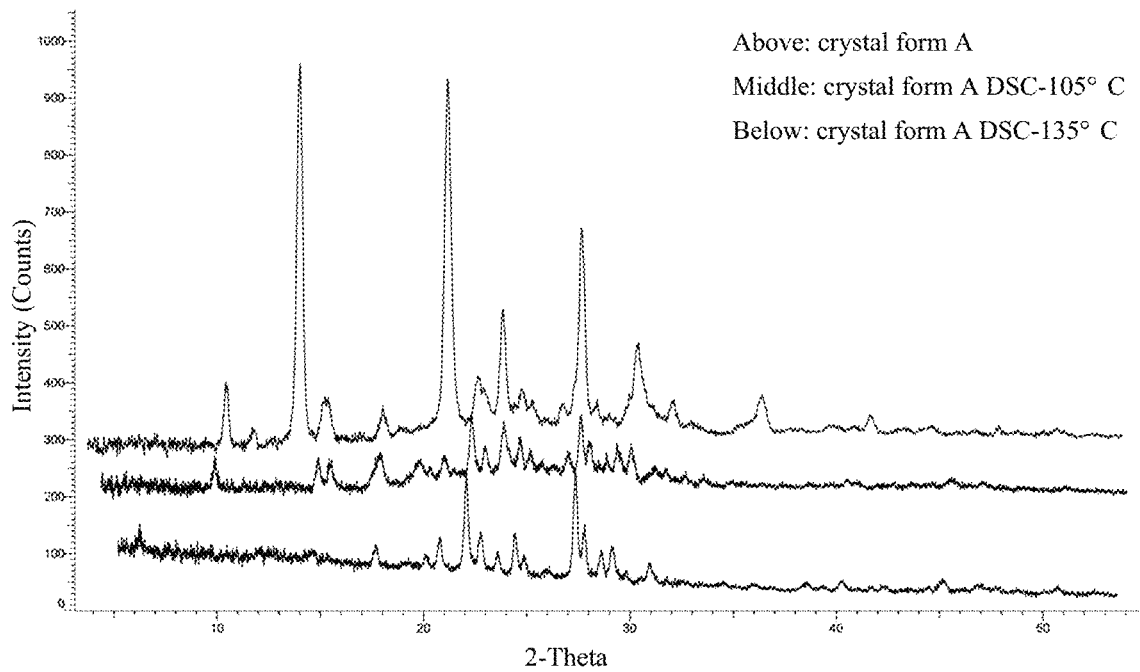
FIG. 18 shows the comparative XRPD spectrum of crystal form A of the compound of formula (I) before and after DSC heating.
Figure 19:
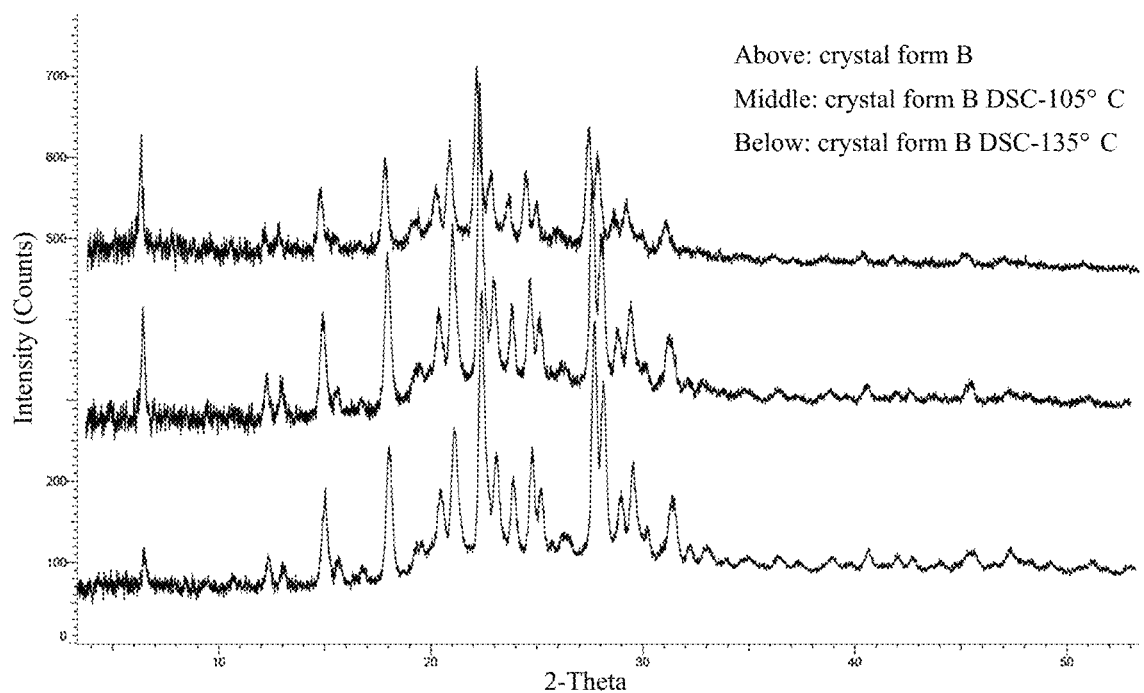
FIG. 19 shows the comparative XRPD spectrum of crystal form B of the compound of formula (I) before and after DSC heating.
Figure 20:
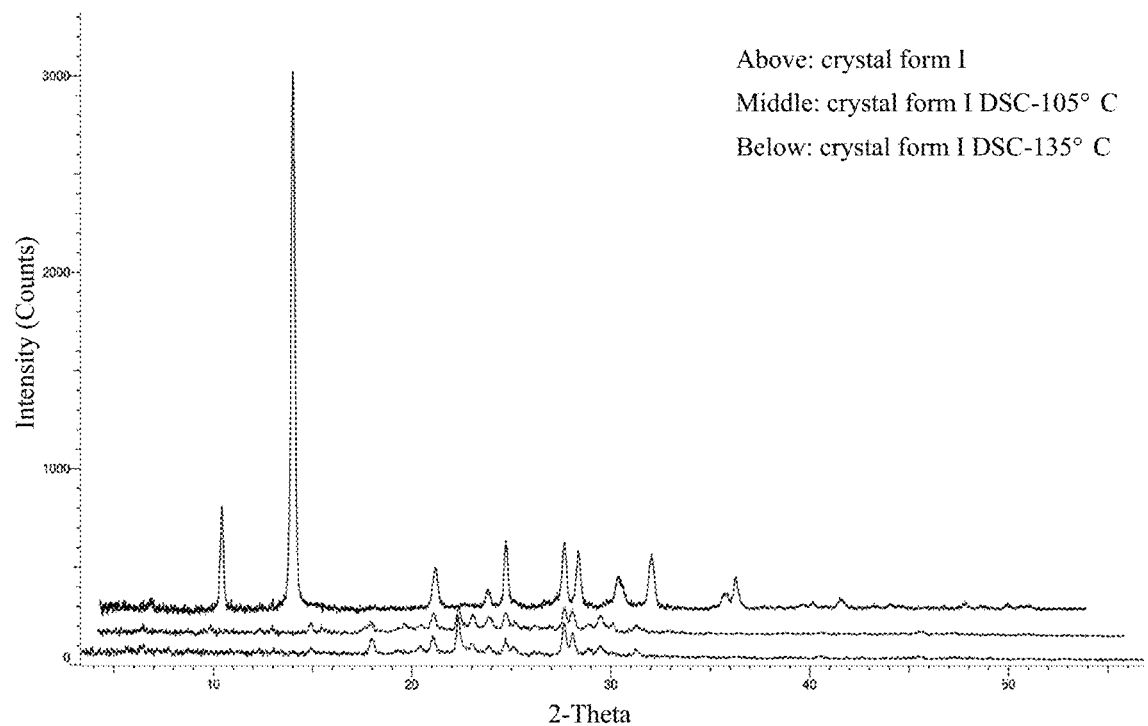
FIG. 20 shows the comparative XRPD spectrum of crystal form I of the compound of formula (I) before and after DSC heating.

XRPD test was carried out on the samples of crystal forms A, B and I after the DSC test. The comparative XRPD spectra of each crystal form are shown in FIGS. 18-20. The results showed that crystal form B did not change after heating to 135° C., indicating that crystal form B is stable; both crystal forms A and I changed after heating to 105° C., indicating that crystal forms A and I are unstable.

Example 10

Figure 21:
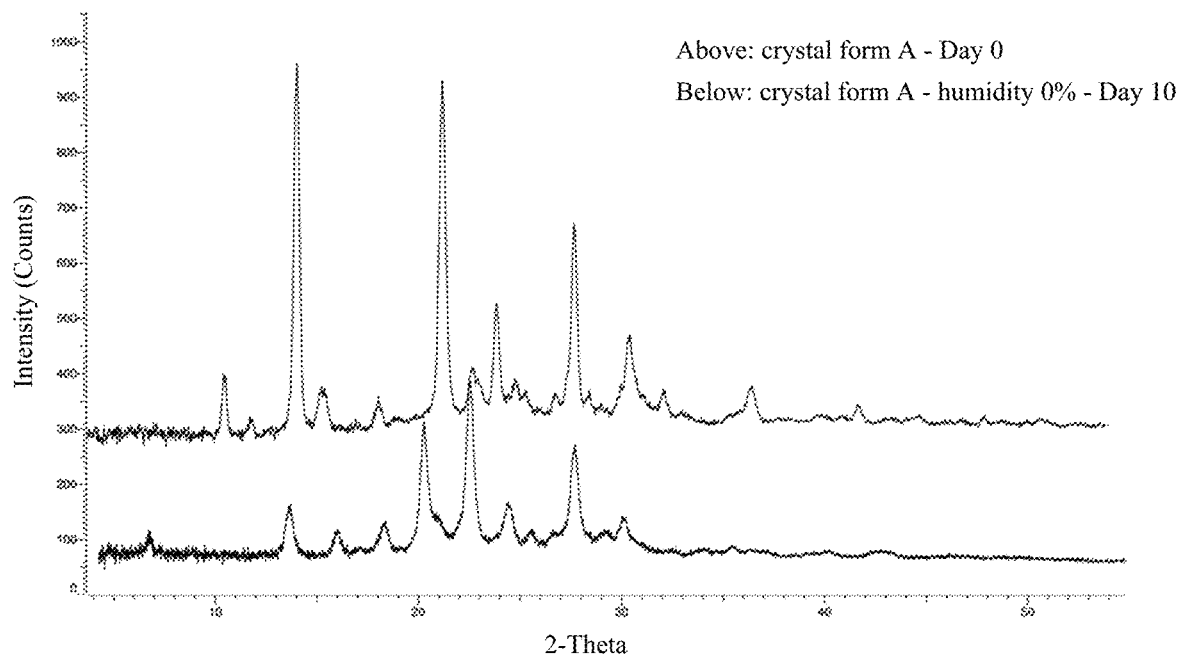
FIG. 21 shows the comparative XRPD spectrum of crystal form A of the compound of formula (I) before and after being left to stand for 10 days under the condition of relative humidity 0%.
Figure 22:
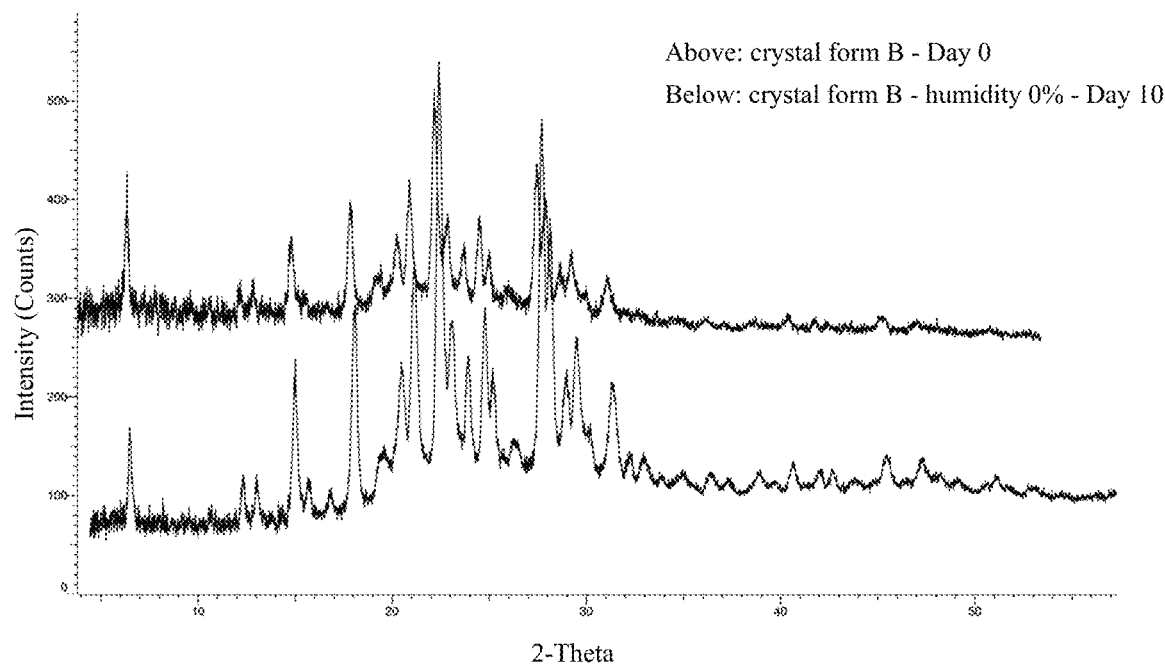
FIG. 22 shows the comparative XRPD spectrum of crystal form B of the compound of formula (I) before and after being left to stand for 10 days under the condition of relative humidity 0%.

The samples of crystal forms A and B were left to stand under the condition of 0% humidity for 10 days, and subjected to XRPD to investigate the stability of the crystal form under the low humidity condition. The comparative XRPD spectra of each crystal form are shown in FIGS. 21-22.

The XRPD results showed that crystal form A changed after being left to stand under the condition of 0% humidity for 10 days, indicating that crystal form A is unstable; crystal form B did not change after being left to stand under the condition of 0% humidity for 10 days, indicating that crystal form B is stable; crystal form B is more stable than crystal form A under the low humidity condition.

Example 11

The samples of crystal forms A, B and I were left to stand under different humidity conditions to test their chemical stability. The results are shown in Table 8. The impurity content was determined by HPLC (HPLC detection conditions: ZORBAX SB-C18 4.6*150 mm 3.5 μm, mobile phase: TFA/methanol/water, detection wavelength: 223 nm).

TABLE 8

Chemical stability of each crystal form

| Placement condition | Time | Total impurity content (%) | | |
|---|---|---|---|---|
| | | Crystal form A | Crystal form B | Crystal form I |
| Day 0 | | 1.88 | 0.95 | 1.56 |
| Humidity 0% (25° C.) | 5 days | 1.89 | 0.97 | 1.57 |
| | 10 days | 2.00 | 1.03 | 1.58 |
| | 30 days | 2.14 | 1.09 | 2.06 |
| Humidity 75% (25° C.) | 5 days | 1.92 | 0.94 | 1.72 |
| | 10 days | 1.97 | 0.98 | 1.78 |
| | 30 days | 2.17 | 1.06 | 1.88 |
| Humidity 92.5% (25° C.) | 5 days | 1.96 | 0.98 | 1.90 |
| | 10 days | 1.99 | 0.98 | 2.24 |
| | 30 days | 2.05 | 1.02 | 2.22 |

It can be seen from Table 8 that crystal form B has a low impurity content, and the content substantially did not increase under various conditions, indicating that crystal form B has a good stability. But, crystal forms A and I have a relatively high impurity content, and the impurity content changed significantly under various conditions.

What is claimed is:
1. A crystal form of a compound of formula (I):

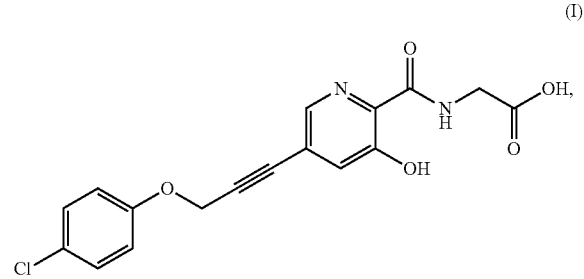 [SMILES: O=C(O)CNC(=O)c1ncc(C#CCOc2ccc(Cl)cc2)cc1O]

selected from the group consisting of crystal form A, crystal form B, crystal form C, crystal form D, crystal form H, and crystal form I, wherein:
the crystal form A has an X-ray powder diffraction spectrum comprising characteristic peaks at diffraction 2θ angles of 10.44, 14.01, 15.27, 18.03, 21.18, 22.66, 22.96, 23.85, 27.68 and 30.37;

the crystal form B has an X-ray powder diffraction spectrum comprising characteristic peaks at diffraction 2θ angles of 6.34, 12.17, 14.75, 17.84, 20.27, 20.89, 22.17, 22.85, 24.49, 27.46, 27.86 and 29.19;

the crystal form C has an X-ray powder diffraction spectrum comprising characteristic peaks at diffraction 2θ angles of 6.33, 9.71, 14.04, 14.70, 17.79, 20.84, 21.19, 22.16, 22.85, 23.68, 24.53, 27.47 and 28.73;

the crystal form D has an X-ray powder diffraction spectrum comprising characteristic peaks at diffraction 2θ angles of 7.28, 9.67, 9.72, 9.79, 14.72, 15.37, 17.67, 19.56, 21.21, 23.79, 26.88 and 29.85;

the crystal form H has an X-ray powder diffraction spectrum comprising characteristic peaks at diffraction 2θ angles of 7.79, 15.69, 16.17, 16.21, 17.54, 19.63, 23.95, 25.59, 25.64 and 31.74; and the crystal form I has an X-ray powder diffraction spectrum comprising characteristic peaks at diffraction 2θ angles of 6.86, 10.44, 14.02, 21.19, 23.82, 24.73, 27.67, 28.37, 30.38, 30.41, 30.51, 32.05, 35.69, 36.28 and 41.55.

2. The crystal form according to claim 1, wherein the crystal form is the crystal form A.

3. The crystal form according to claim 2, wherein the crystal form A has an X-ray powder diffraction spectrum comprising characteristic peaks at diffraction 2θ angles of 10.44, 11.78, 14.01, 15.27, 18.03, 21.18, 22.66, 22.96, 23.85, 24.78, 25.29, 27.68, 30.37 and 36.38.

4. The crystal form according to claim 2, wherein the crystal form A has an X-ray powder diffraction spectrum comprising characteristic peaks at diffraction 2θ angles of 10.44, 11.78, 14.01, 15.27, 18.03, 21.18, 22.66, 22.96, 23.85, 24.78, 25.29, 26.76, 27.68, 28.36, 30.37, 32.07, 36.38 and 41.67.

5. The crystal form according to claim 2, wherein the crystal form A has an X-ray powder diffraction spectrum comprising substantially the same characteristic peaks at diffraction 2θ angles as shown in FIG. 1.

6. The crystal form according to claim 1, wherein the crystal form is the crystal form B.

7. The crystal form according to claim 6, wherein the crystal form B has an X-ray powder diffraction spectrum comprising characteristic peaks at diffraction 2θ angles of 6.34, 12.17, 12.84, 14.75, 17.84, 19.35, 20.27, 20.89, 22.17, 22.85, 23.68, 24.49, 25.03, 27.46, 27.86, 28.54, 29.19 and 31.12.

8. The crystal form according to claim 6, wherein the crystal form B has an X-ray powder diffraction spectrum comprising characteristic peaks at diffraction 2θ angles of 6.34, 12.17, 12.84, 14.75, 17.84, 19.35, 20.27, 20.89, 22.17, 22.85, 23.68, 24.49, 25.03, 26.00, 27.46, 27.86, 28.54, 29.19, 29.99, 31.12, 32.62 and 40.36.

9. The crystal form according to claim 6, wherein the crystal form B has an X-ray powder diffraction spectrum comprising substantially the same characteristic peaks at diffraction 2θ angles as shown in FIG. 2.

10. The crystal form according to claim 1, wherein the crystal form is the crystal form C.

11. The crystal form according to claim 1, wherein the crystal form is the crystal form D.

12. The crystal form according to claim 1, wherein the crystal form is the crystal form H.

13. The crystal form according to claim 1, wherein the crystal form is the crystal form I.

14. A pharmaceutical composition comprising one or more of the crystal forms A, B, C, D, H and I of the compound of formula (I) according to claim 1 and one or more pharmaceutically acceptable carriers, diluents and excipients.

15. The pharmaceutical composition according to claim 14, prepared by mixing one or more of crystal forms A, B, C, D, H and I of the compound of formula (I) with one or more pharmaceutically acceptable carriers, diluents and excipients.

16. A method for preparing the pharmaceutical composition according to claim 14, comprising mixing one or more of crystal forms A, B, C, D, H and I of the compound of formula (I) with one or more pharmaceutically acceptable carriers, diluents and excipients.

17. A method for preparing the crystal form A of the compound of formula (I) according to claim 2, comprising:
(1) dissolving the compound of formula (I) in an appropriate amount of solvent to obtain a mixture, crystallizing the compound of formula (I) from the mixture to obtain a crystal, and filtering the crystal to obtain the crystal form A, wherein the solvent is one or more selected from the group consisting of dimethyl sulfoxide, tetrahydrofuran, propylene glycol methyl ether, methanol, acetonitrile, ethyl acetate, ethanol, water and isopropanol; or
(2) adding the compound of formula (I) into an appropriate amount of solvent to obtain a mixture, slurrying and filtering the mixture to obtain the crystal form A, wherein the solvent is one or more selected from the group consisting of water, cyclohexane, methanol and ethanol.

* * * * *